US010294312B2

(12) United States Patent
Holtcamp et al.

(10) Patent No.: US 10,294,312 B2
(45) Date of Patent: *May 21, 2019

(54) OLEFIN POLYMERIZATION CATALYST SYSTEM COMPRISING MESOPOROUS ORGANOSILICA SUPPORT

(71) Applicant: ExxonMobil Research and Engineering Company, Annandale, NJ (US)

(72) Inventors: Matthew W. Holtcamp, Huffman, TX (US); Gregory S. Day, College Station, TX (US); David F. Sanders, Houston, TX (US); David C. Calabro, Bridgewater, NJ (US); Quanchang Li, Dayton, NJ (US); Machteld M. W. Mertens, Boortmeerbeek (BE)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,513

(22) PCT Filed: Dec. 11, 2015

(86) PCT No.: PCT/US2015/065344
§ 371 (c)(1),
(2) Date: May 12, 2017

(87) PCT Pub. No.: WO2016/094843
PCT Pub. Date: Jun. 16, 2016

(65) Prior Publication Data
US 2017/0327604 A1 Nov. 16, 2017

Related U.S. Application Data

(60) Provisional application No. 62/091,071, filed on Dec. 12, 2014, provisional application No. 62/091,077, filed on Dec. 12, 2014.

(51) Int. Cl.
| | | |
|---|---|---|
| C08F 4/64 | (2006.01) |
| C08F 4/76 | (2006.01) |
| C08F 4/52 | (2006.01) |
| C08F 4/6592 | (2006.01) |
| C07D 251/30 | (2006.01) |
| C08F 4/02 | (2006.01) |
| C08F 210/02 | (2006.01) |
| C08G 77/60 | (2006.01) |

(52) U.S. Cl.
CPC .......... C08F 4/6592 (2013.01); C07D 251/30 (2013.01); C08F 4/02 (2013.01); C08F 210/02 (2013.01); C08G 77/60 (2013.01)

(58) Field of Classification Search
CPC .................... C08F 4/76; C08F 4/64
See application file for complete search history.

(56) References Cited

U.S. PATENT DOCUMENTS

| | | |
|---|---|---|
| 2,653,959 A | 9/1953 | Moore et al. |
| 2,943,105 A | 6/1960 | Caruthers |
| 3,178,392 A | 4/1965 | Kriner |
| 3,248,179 A | 4/1966 | Norwood |
| 3,489,808 A | 4/1967 | Eberly |
| 3,931,350 A | 1/1976 | Sparks |
| 4,218,308 A | 8/1980 | Itoh et al. |
| 4,218,339 A | 8/1980 | Zucchini et al. |
| 4,328,122 A | 5/1982 | Monte et al. |
| 4,337,156 A | 6/1982 | DeRosset |
| 4,395,360 A | 7/1983 | Albizatti et al. |
| 4,473,660 A | 9/1984 | Albizatti et al. |
| 4,530,914 A | 7/1985 | Ewen et al. |
| 4,535,068 A | 8/1985 | Job |
| 4,542,199 A | 9/1985 | Kaminsky et al. |

(Continued)

FOREIGN PATENT DOCUMENTS

| | | |
|---|---|---|
| CN | 101804335 A | 8/2010 |
| CN | 101980013 A | 2/2011 |

(Continued)

OTHER PUBLICATIONS

Bahuleyan, B.K.; Jermy, B.R.; Ahn, I.Y.; Suh, H.; Park, D.-W.; Ha, C.S.; Kim, I. Catalysis Communications 2009, 11, 252-256.*
O'Brien, S.; Tudor, J.; Maschmeyer, T.; O'Hare, D. Chem. Commun. 1997, 1905-1906. (Year: 1997).*
Landskron, K.; Hatton, B.D.; Perovic, D.D.; Ozin, G.. Science Oct. 10, 2003, vol. 302, 266-269. (Year: 2003).*
Wild et al., "Determination of branching distributions in polyethylene and ethylene copolymers", Journal of Polymer Science: Polymer Physics Edition, 1982-03, pp. 441-455, vol. 20, iss. 3, Wiley Online Library.
Liu et al., "Synthesis of Polycarbosilane/Siloxane Hybrid Polymers and their Pyrolytic conversion to Silicon Oxycarbide Ceramics", Chemistry of Materials, Nov. 1, 1997, pp. 2434-2441, vol. 9, No. 11, ACS Publications.

(Continued)

*Primary Examiner* — Rip A Lee
(74) *Attorney, Agent, or Firm* — Liza Negron; Lisa K. Holthus; Amanda K. Norwood

(57) ABSTRACT

A catalyst system comprising a combination of: 1) an activator; 2) one or more metallocene catalyst compounds; 3) a support comprising an organosilica material, which may be a mesoporous organosilica material. The organosilica material may be a polymer of at least one monomer of Formula $[Z^1OZ^2SiCH_2]_3$ (I), where $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group, or an oxygen atom bonded to a silicon atom of another monomer. This invention further relates to processes to polymerize olefins comprising contacting one or more olefins with the above catalyst system.

21 Claims, No Drawings

(56) References Cited

U.S. PATENT DOCUMENTS

| | | |
|---|---|---|
| 4,543,399 A | 9/1985 | Jenkins, III et al. |
| 4,547,552 A | 10/1985 | Toyota et al. |
| 4,562,173 A | 12/1985 | Terano et al. |
| 4,588,790 A | 5/1986 | Jenkins, III et al. |
| 4,613,484 A | 9/1986 | Ayres et al. |
| 4,769,910 A | 9/1988 | Noon |
| 4,808,561 A | 2/1989 | Welborn, Jr. |
| 4,871,705 A | 10/1989 | Hoel |
| 4,933,403 A | 6/1990 | Kaminsky et al. |
| 4,937,299 A | 6/1990 | Ewen et al. |
| 4,990,477 A | 2/1991 | Kioka et al. |
| 4,990,479 A | 2/1991 | Ishimaru et al. |
| 5,008,204 A | 4/1991 | Stehling |
| 5,017,714 A | 5/1991 | Welborn, Jr. |
| 5,026,798 A | 6/1991 | Canich |
| 5,028,670 A | 7/1991 | Chinh et al. |
| 5,041,584 A | 8/1991 | Crapo et al. |
| 5,057,475 A | 10/1991 | Canich et al. |
| 5,096,867 A | 3/1992 | Canich |
| 5,120,867 A | 6/1992 | Welborn, Jr. |
| 5,153,157 A | 10/1992 | Hlatky et al. |
| 5,159,021 A | 10/1992 | Kioka et al. |
| 5,245,107 A | 9/1993 | Yon et al. |
| 5,278,119 A | 1/1994 | Turner et al. |
| 5,304,614 A | 4/1994 | Winter et al. |
| 5,317,036 A | 5/1994 | Brady, III et al. |
| 5,324,800 A | 6/1994 | Welborn, Jr. et al. |
| 5,326,855 A | 7/1994 | Kahn |
| 5,350,723 A | 9/1994 | Neithamer et al. |
| 5,352,749 A | 10/1994 | DeChellis et al. |
| 5,365,003 A | 11/1994 | Chang et al. |
| 5,391,790 A | 2/1995 | Rohrmann et al. |
| 5,405,922 A | 4/1995 | DeChellis et al. |
| 5,436,304 A | 7/1995 | Griffin et al. |
| 5,453,410 A | 9/1995 | Kolthammer et al. |
| 5,453,471 A | 9/1995 | Bernier et al. |
| 5,462,999 A | 10/1995 | Griffin et al. |
| 5,612,271 A | 3/1997 | Zandona |
| 5,616,661 A | 4/1997 | Eisinger et al. |
| 5,630,937 A | 5/1997 | Betz et al. |
| 5,668,228 A | 9/1997 | Chinh et al. |
| 5,719,322 A | 2/1998 | Lansbarkis et al. |
| 5,942,459 A | 8/1999 | Sugano et al. |
| 6,051,631 A | 4/2000 | Hottovy |
| 6,087,459 A | 7/2000 | Miro et al. |
| 6,111,162 A | 8/2000 | Rossini et al. |
| 6,118,037 A | 9/2000 | Piccoli et al. |
| 6,127,303 A | 10/2000 | Ebara et al. |
| 6,133,385 A | 10/2000 | Shamshoum et al. |
| 6,211,105 B1 | 4/2001 | Holtcamp |
| 6,632,766 B2 | 10/2003 | Kanazirev |
| 6,790,344 B1 | 9/2004 | Min et al. |
| 6,987,152 B1 | 1/2006 | Eisinger et al. |
| 7,102,044 B1 | 9/2006 | Kulprathipanja et al. |
| 7,141,630 B2 | 11/2006 | Vizzini et al. |
| 7,141,631 B2 | 11/2006 | Murakami et al. |
| 7,141,632 B2 | 11/2006 | Vaughan et al. |
| 7,300,905 B2 | 11/2007 | Keefer et al. |
| 7,326,821 B2 | 2/2008 | Risch et al. |
| 7,368,618 B2 | 5/2008 | Kulprathipanja et al. |
| 7,427,570 B2 | 9/2008 | Marsh |
| 7,497,965 B2 | 3/2009 | Wariishi et al. |
| 7,538,065 B2 | 5/2009 | McCarthy et al. |
| 7,576,248 B2 | 8/2009 | Kulprathipanja et al. |
| 7,682,502 B2 | 3/2010 | McCarthy et al. |
| 7,705,062 B2 | 4/2010 | Markowitz et al. |
| 7,754,330 B2 | 7/2010 | Hamada et al. |
| 7,767,620 B2 | 8/2010 | Whitnall et al. |
| 7,947,799 B2 | 5/2011 | Manfred et al. |
| 8,110,692 B2 | 2/2012 | Bellussi et al. |
| 8,211,498 B2 | 7/2012 | Ku et al. |
| 8,277,600 B2 | 10/2012 | Hamada et al. |
| 8,277,661 B2 | 10/2012 | Sah et al. |
| 8,425,762 B2 | 4/2013 | McCarthy et al. |
| 8,441,006 B2 | 5/2013 | Michalak et al. |
| 8,470,074 B2 | 6/2013 | Baugh et al. |
| 8,545,694 B2 | 10/2013 | McCarthy et al. |
| 8,562,856 B2 | 10/2013 | Giannantonio et al. |
| 8,568,520 B2 | 10/2013 | Ohashi et al. |
| 8,598,070 B1 | 12/2013 | Baugh et al. |
| 8,598,071 B1 | 12/2013 | Baugh et al. |
| 8,658,556 B2 | 2/2014 | Stewart |
| 8,809,561 B2 * | 8/2014 | Bellussi .................. C01B 37/00 502/407 |
| 9,181,282 B2 | 11/2015 | Ide et al. |
| 2002/0147377 A1 | 10/2002 | Kanazirev |
| 2003/0188991 A1 | 10/2003 | Shan et al. |
| 2005/0093189 A1 | 5/2005 | Vo |
| 2006/0058565 A1 | 3/2006 | De Wild |
| 2006/0070917 A1 | 4/2006 | McCarthy et al. |
| 2006/0173123 A1 | 8/2006 | Yang et al. |
| 2007/0003492 A1 | 1/2007 | Kitahata et al. |
| 2007/0034992 A1 | 2/2007 | Wariishi et al. |
| 2007/0054136 A1 | 3/2007 | Takahashi et al. |
| 2007/0112242 A1 | 5/2007 | Edmiston |
| 2007/0173401 A1 | 7/2007 | Landskron et al. |
| 2009/0130412 A1 | 5/2009 | Hatton et al. |
| 2009/0215612 A1 | 8/2009 | McCarthy et al. |
| 2009/0294922 A1 | 12/2009 | Hamada et al. |
| 2009/0312511 A1 | 12/2009 | Ramage et al. |
| 2010/0155302 A1 | 6/2010 | Kaminsky et al. |
| 2010/0197989 A1 | 8/2010 | Ducreux et al. |
| 2010/0233482 A1 | 9/2010 | Hamada et al. |
| 2011/0079145 A1 | 4/2011 | Dolan et al. |
| 2011/0139685 A1 | 6/2011 | McCarthy et al. |
| 2011/0190115 A1 | 8/2011 | Ciriminna et al. |
| 2011/0281993 A1 | 11/2011 | Pinnavaia et al. |
| 2012/0059181 A1 | 3/2012 | Bellussi et al. |
| 2012/0160742 A1 | 6/2012 | Sohn et al. |
| 2013/0075876 A1 | 3/2013 | Goethals et al. |
| 2013/0078172 A1 | 3/2013 | Bingbing et al. |
| 2013/0249049 A1 | 9/2013 | Michalak et al. |
| 2014/0004358 A1 | 1/2014 | Blackwell et al. |
| 2014/0186246 A1 | 7/2014 | Calabro et al. |
| 2014/0208753 A1 | 7/2014 | Liu et al. |
| 2015/0011787 A1 | 1/2015 | Bellussi et al. |
| 2016/0167015 A1 | 6/2016 | Podsiadlo et al. |
| 2016/0167016 A1 | 6/2016 | Li et al. |
| 2016/0167032 A1 | 6/2016 | Podsiadlo et al. |
| 2016/0168171 A1 | 6/2016 | Li et al. |
| 2016/0168172 A1 | 6/2016 | Li et al. |
| 2016/0168173 A1 | 6/2016 | Li et al. |
| 2016/0168174 A1 | 6/2016 | Li et al. |
| 2016/0168333 A1 | 6/2016 | Podsiadlo et al. |
| 2016/0168484 A1 | 6/2016 | Weigel et al. |
| 2016/0168485 A1 | 6/2016 | Li et al. |
| 2016/0229959 A1 | 8/2016 | Li et al. |
| 2017/0306065 A1 * | 10/2017 | Holtcamp ............. C08F 210/02 |
| 2017/0313791 A1 | 11/2017 | Mertens et al. |
| 2017/0320971 A1 * | 11/2017 | Holtcamp ........... C08F 4/65916 |
| 2017/0320977 A1 * | 11/2017 | Holtcamp ............... C08F 10/02 |
| 2017/0327604 A1 * | 11/2017 | Holtcamp ............. C08F 4/6592 |
| 2017/0354961 A1 | 12/2017 | Podsiadlo et al. |
| 2017/0355822 A1 | 12/2017 | Calabro et al. |
| 2017/0355823 A1 | 12/2017 | Peterson et al. |
| 2018/0142066 A1 | 5/2018 | Falkowski et al. |

FOREIGN PATENT DOCUMENTS

| | | |
|---|---|---|
| CN | 102052713 A | 5/2011 |
| CN | 102643429 A | 8/2012 |
| CN | 103495340 A | 1/2014 |
| CN | 103613975 A | 3/2014 |
| CN | 104117343 A | 10/2014 |
| CN | 103157362 A | 6/2016 |
| EP | 1022056 A1 | 7/2000 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |

(56) References Cited

FOREIGN PATENT DOCUMENTS

| | | |
|---|---|---|
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9407928 A1 | 4/1994 |
| WO | 9514044 A1 | 5/1995 |
| WO | 9610537 A1 | 4/1996 |
| WO | 9843983 A1 | 10/1998 |
| WO | 9940125 A1 | 8/1999 |
| WO | 0044795 A1 | 8/2000 |
| WO | 2004106391 A1 | 12/2004 |
| WO | 2006032140 A1 | 3/2006 |
| WO | 2007081212 A1 | 7/2007 |
| WO | 2008010962 A2 | 1/2008 |
| WO | 2008013519 A2 | 1/2008 |
| WO | 2011003805 A2 | 1/2011 |
| WO | 2011145933 A1 | 11/2011 |
| WO | 2013093022 A1 | 6/2013 |
| WO | 2014040512 A1 | 1/2014 |
| WO | 2014090757 A1 | 6/2014 |
| WO | 2015100198 A1 | 7/2015 |
| WO | 2016094784 A1 | 6/2016 |
| WO | 2016094803 A1 | 6/2016 |

OTHER PUBLICATIONS

Oliveira et al., "High-Pressure Phase Equilibria for Polypropylene-Hydrocarbon Systems", Industrial & Engineering Chemistry Research, 2000, pp. 4627-4633, vol. 39 (12), ACS Publications.
Van Der Voort et al., "Periodic Mesoporous Organosilicas: from simple to complex bridges; a comprehensive Overview of functions, morphologies and applications", Chemical Society Reviews, 2013, pp. 3913-3955, vol. 42, Royal Society of Chemistry.
Vasconcellos-Dias et al., "Heptacoordinate tricarbonyl Mo(II) complexes as highly selective oxidation homogeneous and heterogeneous catalysts", Journal of Catalysis, Jun. 10, 2008, pp. 301-311, vol. 256, iss. 2, ScienceDirect.
Alt et al., "Polymerization of ethylene with metallocene/methylaluminoxane catalysts supported on polysiloxane micro gels and silica", Journal of Organometallic Chemistry, Oct. 15, 1998, pp. 263-269, vol. 568, No. 1-2, ScienceDirect.
PCT/US2015/065344 International Search Report and Written Opinion dated Jun. 20, 2016.
Topchiev et al., "Preparation of hexa alkoxy derivatives of cyclotrimethylenesilane", Doklady Akademii Nauk SSSR, 1955, pp. 95-96. vol. 103.
Kriner, "The preparation of cyclic siliconmethylene compounds", Journal of Organic Chemistry, Jun. 1964, pp. 1601-1606, vol. 29.
Kuivila et al., "Trimethylsilyl-substituted norbornenes, norbornanes, and nortricyclene", Journal of Organic Chemistry, Oct. 1964, pp. 2845-2851, vol. 29.
Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.
Inagari et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.
Melde et al., "Mesoporous Sieves with Unified Hybrid Inorganic/Organic Frameworks", Chemistry of Materials, Oct. 9, 1999, pp. 3302-3308, vol. 11.
Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
"Vidal et al., ""Adsorption of polycyclic aromatic hydrocarbons from aqueous solutions by modified periodic mesoporous organosilica""", Journal of Colloid and Interface Science, Feb. 3, 2011, pp. 466-473, vol. 357, No. 2."
Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
"Poli et al., ""Different Routes for Preparing Mesoporous Organosilicas Containing the Troger's Base and Their Textural and Catalytic Implications"", The Journal of Physical Chemistry C,Apr. 21, 2011, pp. 7573-7585, vol. 115, No. 15, ACS Publications."
PCT/US2015/065208 International Search Report and Written Opinion dated May 17, 2016.
PCT/US2015/065200 Partial International Search Report and Written Opinion dated May 23, 2016.
"Diaz et al., ""Hybrid organic-inorganic catalytic porous materials synthesized at neutral pH in absence of structural directing agents""", Journal of Materials Chemistry, Jan. 1, 2009, pp. 5970-5979, vol. 19, No. 33, Royal Society of Chemistry."
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Goethals et al., "Ultra-low-k cyclic carbon-bridged PMO films with a high chemical resistance", Journal of Materials Chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Eliseeva et al., "Antifoaming additive for alkaline absorption solutions for removal of carbon dioxide from synthesis gas", Khimicheskaya Promyshlennost, 1999, pp. 632-633, vol. 10.
Brondani et al., "Polyfunctional carbosilanes and organosilicon compounds. Synthesis via Grignard reactions", Tetrahedron Letters, 1993, pp. 2111-2114, vol. 34.

(56) References Cited

OTHER PUBLICATIONS

Gilman et al., "Reactions of triphenylsilyllithium with some dichloropropenes", Journal of Organometallic Chemistry, Apr. 13, 2001, pp. 293-303, vol. 2.
Goethals, et al., "A new procedure to seal the pores of mesoporous low-k films with precondensed organosilica oligomers", Chemical Communications, 2012, pp. 2797-2799, vol. 48, No. 22, Royal Society of Chemistry.
Goethals et al., "Sealed ultra low-k organosilica films with improved electrical, mechanical and chemical properties", Journal of Materials Chemistry C, 2013, vol. 1, No. 25, Royal Society of Chemistry.
Goethals et al., "Hydrophobic high quality ring PMOs with an extremely high stability", Journal of Materials Chemistry, 2010, pp. 1709-1716, vol. 20, No. 9, Royal Society of Chemistry.
Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.
Landskron et al., "Periodic Mesoporous Organosilicas Containing Interconnected [Si(CH2)]3 Rings", Science, Oct. 10, 2003, pp. 266-269, vol. 302.
Bahuleyan et al., "One-pot synthesis of spherical periodic mesoporous organosilica supported catalyst bearing Ni(II) α-diimine complexes for ethylene polymerization", Catalysis Communications, 2009, pp. 252-256, vol. 11.
O'Brien S., et al., "EXAFS analysis of a chiral alkene polymerization catalyst incorporated in the mesoporous silicate MCM-41" Chem. Comm. 1905-1906 (1997).

* cited by examiner

OLEFIN POLYMERIZATION CATALYST SYSTEM COMPRISING MESOPOROUS ORGANOSILICA SUPPORT

CROSS-REFERENCE TO RELATED APPLICATIONS

This application is a National Stage Application of International Application No. PCT/US2015/065344, filed Dec. 11, 2015 and claims the benefit of and priority to U.S. Provisional Application No. 62/091,071 filed on Dec. 12, 2014 and U.S. Provisional Application No. 62/091,077 filed on Dec. 12, 2014. The entire disclosures of each of the above applications are fully incorporated herein by reference.

FIELD OF THE INVENTION

The present disclosure relates to novel olefin polymerization catalyst compositions comprising olefin polymerization catalyst compound, optional activator, and organosilica material support, and uses thereof.

BACKGROUND OF THE INVENTION

Supported olefin polymerization catalysts are of great use in industry. Hence, there is interest in finding new supported catalyst systems that increase the commercial usefulness of the catalyst and allow the production of polymers having improved properties.

Catalysts for olefin polymerization are often based on cyclopentadienyl based transition metal compounds as catalyst precursors, which are activated either with alumoxane or with an activator containing a non-coordinating anion.

Porous inorganic solids have found great utility as catalysts and separation media for industrial application. In particular, mesoporous materials, such as silicas and aluminas, having a periodic arrangement of mesopores are attractive materials for use in adsorption, separation and catalytic processes due to their uniform and tunable pores, high surface areas and large pore volumes. The pore structure of such mesoporous materials is large enough to adsorb large molecules and the pore wall structure can be as thin as about 1 nm. Further, such mesoporous materials are known to have large specific surface areas (e.g., 1000 m$^2$/g) and large pore volumes (e.g., 1 cc/g). For these reasons, such mesoporous materials enable reactive catalysts, adsorbents composed of a functional organic compound, and other molecules to rapidly diffuse into the pores and therefore, can be advantageous over zeolites, which have smaller pore sizes. Consequently, such mesoporous materials can be useful not only for catalysis of high-speed catalytic reactions, but also as large capacity adsorbents.

Mesoporous organosilica (MOS) supports are conventionally formed by the self-assembly of a silsequioxane precursor in the presence of a structure directing agent, porogen and/or framework element. The precursor is hydrolysable and condenses around the structure directing agent. For example, Landskron, K., et al. report the self-assembly of 1,3,5-tris[diethoxysila]cyclohexane [(EtO)$_2$SiCH$_2$]$_3$ in the presence of a base and the structure directing agent, cetyltrimethylammonium bromide. Landskron, K., et al., Science, 302:266-269 (2003).

However, the use of a structure directing agent, such as a surfactant, in the preparation of an organosilica material, such as a MOS, requires a more complicated, energy intensive process that limits the ability to scale-up the process for industrial applications. Additionally, structure directing agents present during formation impact the morphology of the organosilica material product. Furthermore, introduction of additional agents or processing steps to remove structure directing agents from MOS can introduce additional reactive and undesirable compositions into the system, potentially leading to additional species that could cause catalyst poisoning.

There remains a need in the art for new and improved supported catalysts and catalyst systems for the polymerization of olefins to obtain new and improved polyolefins, polymerization processes, and the like. Such new and improved catalyst systems can desirably achieve specific polymer properties, such as high melting point, high molecular weights, increasing conversion or comonomer incorporation, or altering comonomer distribution without deteriorating the resulting polymer's properties. Thus, there is a need to provide organosilica materials having desirable pore size, pore volume and surface area, which can be prepared in the absence of a structure directing agent, a porogen and/or a framework element (aside from C, O, Si and hydrogen). Such materials will be described further herein. For more information, see also, U.S. Provisional Application No. 62/091,071 filed on Dec. 12, 2014 and U.S. Provisional Application No. 62/091,077 filed on Dec. 12, 2014, the disclosures of which were fully incorporated herein by reference above. Accordingly, new and improved supported catalyst systems for the polymerization of olefins are contemplated by the present disclosure, in order to achieve enhanced properties, such as molecular weight, and/or comonomer incorporation, typically along with improvements in catalyst function, such as activity, by way of non-limiting example.

SUMMARY OF THE INVENTION

This invention relates to a catalyst system comprising the combination of: one or more olefin polymerization catalyst compounds; (2) a support comprising an organosilica material; and (iii) an optional activator. The organosilica material may be a polymer of at least one monomer of Formula [Z$^1$OZ$^2$SiCH$_2$]$_3$, wherein Z$^1$ represents a hydrogen atom, a C$_1$-C$_4$ alkyl group, or a bond to a silicon atom of another monomer and Z$^2$ represents a hydroxyl group, a C$_1$-C$_4$ alkoxy group, a C$_1$-C$_6$ alkyl group or an oxygen atom bonded to a silicon atom of another monomer.

In certain aspects, this invention relates to a catalyst system comprising: at least one metallocene compound; (2) a catalyst support comprising an organosilica material that is a polymer of at least one monomer of Formula [Z$^1$OZ$^2$SiCH$_2$]$_3$ (I), wherein Z$^1$ represents a hydrogen atom, a C$_1$-C$_4$ alkyl group, or a bond to a silicon atom of another monomer and Z$^2$ represents a hydroxyl group, a C$_1$-C$_4$ alkoxy group, a C$_1$-C$_6$ alkyl group, or an oxygen atom bonded to a silicon atom of another monomer; and (3) an activator.

In other aspects, the invention relates to a process to produce a polymer comprising: i) contacting, in the gas phase or slurry phase, one or more olefin monomers, with a catalyst system. The catalyst system comprises: 1) one or more olefin polymerization catalyst compounds; 2) a catalyst support comprising an organosilica material that is a polymer of at least one monomer of Formula [Z$^1$OZ$^2$SiCH$_2$]$_3$ (I), wherein Z$^1$ represents a hydrogen atom, a C$_1$-C$_4$ alkyl group, or a bond to a silicon atom of another monomer and Z$^2$ represents a hydroxyl group, a C$_1$-C$_4$ alkoxy group, a C$_1$-C$_6$ alkyl group, or an oxygen atom bonded to a silicon atom of another monomer; and 3) an optional activator. The process further comprises ii) obtaining a polymer.

DETAILED DESCRIPTION

In certain aspects, the present disclosure is directed to catalyst systems. The catalyst systems according to certain aspects of the present invention(s) are suitable for use in a polyolefin polymerization reaction process.

The catalyst system may comprise (i) a support comprising an organosilica material; (ii) one or more catalyst metals or compounds; and (iii) an activator, for example, comprising alumoxane or a non-coordinating anion. The organosilica material may be a polymer of at least one monomer of Formula $[Z^1OZ^2SiCH_2]_3$, where $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group or an oxygen atom bonded to a silicon atom of another monomer.

The one or more catalyst compounds are coordination polymerization catalyst compounds, such as Ziegler-Natta catalyst compounds or metallocene catalyst compounds as will be discussed further herein. Useful catalysts include metallocene catalyst compounds represented by the formula:

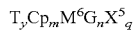

wherein each Cp is, independently, a cyclopentadienyl group (such as cyclopentadiene, indene or fluorene) which may be substituted or unsubstituted, $M^6$ is a Group 4 transition metal, for example, titanium, zirconium, hafnium, G is a heteroatom group represented by the formula $JR^*_z$ where J is N, P, O or S, and $R^*$ is a $C_1$ to $C_{20}$ hydrocarbyl group and z is 1 or 2, T is a bridging group, and y is 0 or 1, $X^5$ is a leaving group (such as a halide, a hydride, an alkyl group, an alkenyl group or an arylalkyl group), and m=1 or 2, n=0, 1, 2 or 3, q=0, 1, 2 or 3, and the sum of m+n+q is equal to the oxidation state of the transition metal.

Definitions

For purposes of this invention and the claims hereto, the numbering scheme for the Periodic Table Groups is according to the IUPAC Periodic Table of Elements.

The terms "substituent," "radical," "group," and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The terms "hydrocarbyl radical," "hydrocarbyl," "hydrocarbyl group," "alkyl radical," and "alkyl" are used interchangeably throughout this document. Likewise, the terms "group," "radical," and "substituent," are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted hydrocarbyl radicals are radicals in which at least one hydrogen atom of the hydrocarbyl radical has been substituted with at least one heteroatom or heteroatom containing group, such as halogen (such as Br, Cl, F or I) or at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like, or where at least one heteroatom has been inserted within a hydrocarbyl ring.

As used herein, and unless otherwise specified, the term "alkyl" refers to a saturated hydrocarbon radical having from 1 to 12 carbon atoms (i.e., $C_1$-$C_{12}$ alkyl), particularly from 1 to 8 carbon atoms (i.e., $C_1$-$C_8$ alkyl), particularly from 1 to 6 carbon atoms (i.e., $C_1C_6$ alkyl), and particularly from 1 to 4 carbon atoms (i.e., $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and "$C_4$ alkyl" refers to butyl (e.g., —$CH_2CH_2CH_2CH_3$, —($CH_3$)$CHCH_2CH_3$, —$CH_2CH$($CH_3$)$_2$, etc.). Further, as used herein, "Me" refers to methyl, and "Et" refers to ethyl, "i-Pr" refers to isopropyl, "t-Bu" refers to tert-butyl, and "Np" refers to neopentyl.

As used herein, and unless otherwise specified, the term "alkylene" refers to a divalent alkyl moiety containing 1 to 12 carbon atoms (i.e., $C_1$-$C_{12}$ alkylene) in length and meaning the alkylene moiety is attached to the rest of the molecule at both ends of the alkyl unit. For example, alkylenes include, but are not limited to, —$CH_2$—, —$CH_2CH_2$—, —$CH(CH_3)CH_2$—, —$CH_2CH_2CH_2$—, etc. The alkylene group may be linear or branched.

As used herein, and unless otherwise specified, the term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e., $C_1$-$C_{12}$ nitrogen-containing alkyl), particularly from 1 to 10 carbon atoms (i.e., $C_1$-$C_{10}$ nitrogen-containing alkyl), particularly from 2 to 10 carbon atoms (i.e., $C_2$-$C_{10}$ nitrogen-containing alkyl), particularly from 3 to 10 carbon atoms (i.e., $C_3$-$C_{10}$ nitrogen-containing alkyl), and particularly from 3 to 8 carbon atoms (i.e., $C_1$-$C_{10}$ nitrogen-containing alkyl). Examples of nitrogen-containing alkyls include, but are not limited to,

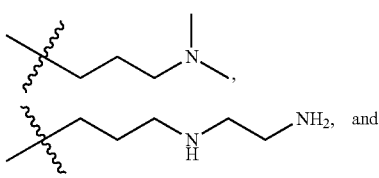

-continued

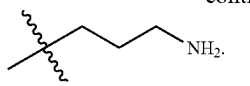

As used herein, and unless otherwise specified, the term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e., $C_1$-$C_{12}$ nitrogen-containing alkylene), particularly from 2 to 10 carbon atoms (i.e., $C_2$-$C_{10}$ nitrogen-containing alkylene), particularly from 3 to 10 carbon atoms (i.e., $C_3$-$C_{10}$ nitrogen-containing alkylene), particularly from 4 to 10 carbon atoms (i.e., $C_4$-$C_{10}$ nitrogen-containing alkylene), and particularly from 3 to 8 carbon atoms (i.e., $C_3$-$C_8$ nitrogen-containing alkyl). Examples of nitrogen-containing alkylenes include, but are not limited to,

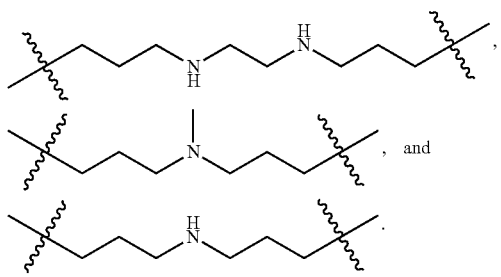

, and

As used herein, and unless otherwise specified, the term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

As used herein, and unless otherwise specified, the term "alkenylene" refers to a divalent alkenyl moiety containing 2 to about 12 carbon atoms (i.e., $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH=CH—, —CH$_2$CH$_2$CH=CHCH$_2$—, etc. The alkenylene group may be linear or branched.

As used herein, and unless otherwise specified, the term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompasses 2-butynyl, and 1,3-butadiynyl and propynyl encompasses 1-propynyl and 2-propynyl (propargyl).

As used herein, and unless otherwise specified, the term "alkynylene" refers to a divalent alkynyl moiety containing 2 to about 12 carbon atoms (i.e., $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—. The alkynylene group may be linear or branched.

As used herein, and unless otherwise specified, the term "alkoxy" refers to —O-alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

As used herein, and unless otherwise specified, the term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

As used herein, and unless otherwise specified, the term "aryl" refers to any monocyclic or polycyclic cyclized carbon radical containing 6 to 14 carbon ring atoms, wherein at least one ring is an aromatic hydrocarbon. Likewise heteroaryl means an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics. Examples of aryls include, but are not limited to phenyl, naphthyl, pyridinyl, indolyl, 2-methyl-phenyl, xylyl, and 4-bromo-xylyl.

As used herein, and unless otherwise specified, the term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl."

Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

As used herein, and unless otherwise specified, the term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

As used herein, and unless otherwise specified, the term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

The term "ring atom" means an atom that is part of a cyclic ring structure. By this definition, a benzyl group has six ring atoms and tetrahydrofuran has 5 ring atoms.

For purposes of this invention and claims thereto, unless otherwise indicated, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

Unless otherwise indicated, where isomers of a named alkyl, alkenyl, alkoxy, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

As used herein, the term "hydroxyl" refers to an —OH group.

As used herein, "oxygenate" refers to a saturated, unsaturated, or polycyclic cyclized hydrocarbon radical containing from 1 to 40 carbon atoms and further containing one or more oxygen heteroatoms.

As used herein, "aluminum alkyl adducts" refers to the reaction product of aluminum alkyls and/or alumoxanes with quenching agents, such as water and/or methanol.

As used herein, the term "mesoporous" refers to solid materials having pores that have a diameter within the range of from about 2 nm to about 50 nm.

As used herein, the term "organosilica" refers to an organosiloxane compound that comprises one or more organic groups bound to two or more Si atoms.

As used herein, the term "silanol" refers to a Si—OH group, and the term "silanol content" refers to the percent of the Si—OH groups in a compound and can be calculated by standard methods, such as NMR.

As used herein, the terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer.

A "polymer" has two or more of the same or different mer units. A "homopolymer" is a polymer having mer units that are the same. A "copolymer" is a polymer having two or more mer units that are distinct or different from each other. A "terpolymer" is a polymer having three mer units that are distinct or different from each other. "Distinct" or "different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

As used herein, $M_n$ is number average molecular weight, $M_w$ is weight average molecular weight, and $M_z$ is z average molecular weight, wt % is weight percent, and mol % is mole percent. Molecular weight distribution (MWD), also referred to as polydispersity (PDI), is defined to be $M_w$ divided by $M_n$. Unless otherwise noted, all molecular weight units (e.g., $M_w$, $M_n$, $M_z$) are g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane, dme is 1,2-dimethoxyethane, TMS is trimethylsilyl, TIBAL is triisobutylaluminum, TNOAL is tri(n-octyl)aluminum, THF (also referred to as the is tetrahydrofuran, RT is room temperature (and is 25° C. unless otherwise indicated), tol is toluene, EtOAc is ethyl acetate, Np is neopentyl, and Cy is cyclohexyl.

Ethylene is considered an α-olefin for purposes of certain aspects of the present disclosure. An oligomer is a polymer having a low molecular weight, such as $M_n$ of less than 25,000 g/mol, or less than 2,500 g/mol, or a low number of mer units, such as 75 mer units or less or 50 mer units or less.

The term "continuous" means a system that operates without interruption or cessation. For example a continuous process to produce a polymer would be one where the reactants are continually introduced into one or more reactors and polymer product is continually withdrawn.

A "solution polymerization" means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng. Chem. Res. 29, 2000, 4627.

A "bulk polymerization" means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

A "catalyst system" is the combination of at least one catalyst compound, an organosilica support material, an optional activator, and an optional co-activator. For the purposes of this invention and the claims thereto, when catalyst systems are described as comprising neutral stable forms of the components, it is well understood by one of ordinary skill in the art, that the ionic form of the component is the form that reacts with the monomers to produce polymers. For example, when "catalyst system" is used to describe a catalyst/activator/support combination before activation, it means the unactivated catalyst complex (precatalyst) together with an activator, support and, optionally, a co-activator. When it is used to describe such after activation, it means the support, the activated complex, and the activator or other charge-balancing moiety. The transition metal compound may be neutral as in a precatalyst, or a charged species with a counter ion as in an activated catalyst system.

Coordination polymerization is an addition polymerization in which successive monomers are added to the organometallic active center.

The terms "cocatalyst" and "activator" are used herein interchangeably and are defined to be any compound which can activate any one of the catalyst compounds herein by converting the neutral catalyst compound to a catalytically active catalyst compound cation.

Organosilica Materials

In certain aspects, the invention relates to organosilica materials used as catalyst support materials. The organosilica material supports may be a polymer formed of at least one monomer, as will be described further below. In certain variations, the organosilica material may be a polymer formed of multiple distinct monomers.

Monomers of Formula (I)

In a first embodiment, the organosilica material supports may be a polymer of at least one monomer of Formula $[Z^1OZ^2SiCH_2]_3$ (I), where $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group, or an oxygen atom bonded to a silicon atom of another monomer.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of another monomer so there may be a bond directly to the silicon atom of the another monomer thereby connecting the two monomers, e.g., via a Si—O—Si linkage. As used herein, and unless otherwise specified, "an oxygen atom bonded to a silicon atom of another monomer" means that the oxygen atom can advantageously displace a moiety (particularly an oxygen-containing moiety such as a hydroxyl), if present, on a silicon atom of the another monomer so the oxygen atom may be bonded directly to the silicon atom of the another monomer thereby connecting the two monomers, e.g., via a Si—O—Si linkage. For clarity, in the aforementioned bonding scenarios, the "another monomer" can be a monomer of the same type or a monomer of a different type.

In various embodiments, each $Z^1$ can be a hydrogen atom. Each $Z^1$ can be a $C_1$-$C_4$ alkyl group, a $C_1$-$C_3$ alkyl group, a $C_1$-$C_2$ alkyl group, or methyl. Each $Z^1$ can be bonded to a silicon atom of another monomer. Each $Z^1$ can be a hydrogen atom, a $C_1$-$C_2$ alkyl group, or a bond to a silicon atom of another monomer. Each $Z^2$ can be a hydroxyl group. Each $Z^2$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, or methyl. Each $Z^2$ can be a $C_1$-$C_4$ alkoxy group, a $C_1$-$C_3$ alkoxy group, a $C_1$-$C_2$ alkoxy group, or methoxy. Each $Z^2$ can be an oxygen atom bonded to a silicon atom of another monomer. Each $Z^2$ can be a hydroxyl group, a $C_1$-$C_4$ alkoxy group, or an oxygen atom bonded to a silicon atom of another monomer. Each $Z^2$ can be a hydroxyl group, a $C_1$-$C_2$ alkyl group (methyl or ethyl), a $C_1$-$C_2$ alkoxy group (methoxy or ethoxy), or an oxygen atom bonded to a silicon atom of another monomer. Each $Z^1$ can be a hydrogen atom, a $C_1$-$C_2$ alkyl group, or a bond to a silicon atom of another monomer and $Z^2$ can be a hydroxyl group, a $C_1$-$C_2$ alkyl group, a $C_1$-$C_2$ alkoxy group, or an oxygen atom bonded to a silicon atom of another monomer. In another embodiment, each $Z^1$ can be a hydrogen atom, ethyl or a bond to a silicon atom of another monomer and each $Z^2$ can be a hydroxyl group, ethoxy, or an oxygen atom bonded to a silicon atom of another monomer. In another embodiment, each $Z^1$ can be a hydrogen atom, ethyl or a bond to a silicon atom of another monomer and each $Z^2$ can be methyl.

In certain variations, the organosilica material may be a polymer of at least one monomer of Formula (I) and also further comprises at least one additional monomer of Formula (I). For example, the polymer may comprise a first monomer of Formula (I), as well as a second distinct monomer of Formula (I).

In a particular embodiment, the polymer may comprise a first monomer of Formula (I), wherein each $Z^1$ can be a hydrogen atom, ethyl or a bond to a silicon atom of another monomer and each $Z^2$ can be a hydroxyl group, ethoxy, or an oxygen atom bonded to a silicon atom of another monomer; and second distinct monomer of Formula (I), wherein each $Z^1$ can be a hydrogen atom, ethyl or a bond to a silicon atom of another monomer and each $Z^2$ can be methyl.

Monomers of Formula (II)

In certain other aspects, the organosilica material support may be a polymer formed of multiple distinct monomers, including a monomer of Formula I in combination with one or more additional monomers.

In a second embodiment, the organosilica material support may be a polymer of at least one monomer of Formula (I) and a monomer of Formula $Z^3OZ^4Z^5Z^6Si$ (II), where $Z^3$ independently represents a hydrogen atom or a $C_1$-$C_4$ alkyl group, or a bond to a silicon atom of another monomer; and each of $Z^4$, $Z^5$ and $Z^6$ are independently selected from the group consisting of a hydroxyl group, a $C_1$-$C_4$ alkyl group (preferably methyl, ethyl, propyl, or butyl), a $C_1$-$C_4$ alkoxy group (preferably methoxy, ethoxy, proposy or butoxy), a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

In various aspects, each $Z^3$ can be a $C_1$-$C_3$ alkyl group, a $C_1$-$C_2$ alkyl group (preferably ethyl, methyl, propyl, butyl) or a bond to a silicon atom of another monomer, and/or each $Z^4$, $Z^5$ and $Z^6$ each independently can be a hydroxyl group. Alternately each $Z^3$ can be a hydrogen atom, a $C_1$-$C_2$ alkyl group, or a bond to a silicon atom of another monomer and $Z^4$, $Z^5$ and $Z^6$ each independently can be a hydroxyl group or a $C_1$-$C_2$ alkyl group.

Each $Z^4$, $Z^5$ and $Z^6$ independently can be a $C_1$-$C_4$ alkyl group, a $C_1$-$C_3$ alkyl group, a $C_1$-$C_2$ alkyl group, or methyl, preferably a hydroxyl group, or a $C_1$-$C_2$ alkyl group, alternately each $Z^4$, $Z^5$ and $Z^6$ independently can be a $C_1$-$C_4$ alkoxy group, a $C_1$-$C_3$ alkoxy group, a $C_1$-$C_2$ alkoxy group, or methoxy, preferably each $Z^4$, $Z^5$ and $Z^6$ is independently can be selected from the group consisting of a hydroxyl group, a $C_1$-$C_2$ alkyl group and a $C_1$-$C_2$ alkoxy group.

Alternately, each $Z^3$ can be a hydrogen atom, a $C_1$-$C_2$ alkyl group, or a bond to a silicon atom of another monomer; and $Z^4$, $Z^5$ and $Z^6$ each independently can be selected from the group consisting of a hydroxyl group, a $C_1$-$C_2$ alkyl group and a $C_1$-$C_2$ alkoxy group.

Each $Z^4$, $Z^5$ and $Z^6$ each independently can be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^4$, $Z^5$ and $Z^6$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

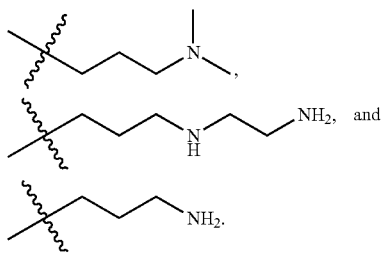

Each $Z^4$, $Z^5$ and $Z^6$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group, a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.), preferably $Z^4$, $Z^5$ and $Z^6$ each independently be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Each $Z^4$, $Z^5$ and $Z^6$ each independently can be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

In a particular embodiment, each $Z^3$ can be a hydrogen atom, ethyl or a bond to a silicon atom of another monomer; and $Z^4$, $Z^5$ and $Z^6$ each independently can be selected from the group consisting of a hydroxyl group, ethoxy, and an oxygen atom bonded to a silicon atom of another monomer.

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be methyl.

In another particular embodiment, each $Z^3$ can be a hydrogen atom, methyl or a bond to a silicon atom of another comonomer; $Z^4$ and $Z^5$ each independently can be selected from the group consisting of a hydroxyl group, methoxy, and an oxygen atom bonded to a silicon atom of another monomer; and $Z^6$ can be

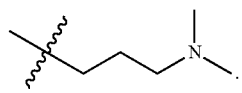 [SMILES: *CCCN(C)C]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

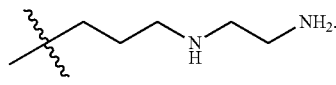 [SMILES: *CCCNCCN]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

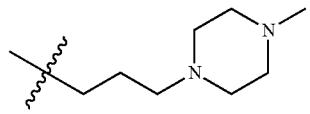

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

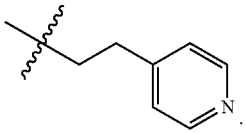 [SMILES: *CCc1ccncc1]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

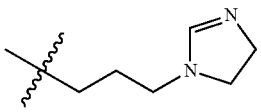

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

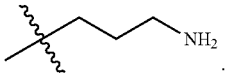 [SMILES: *CCCN]

Monomers of Formula (III)

In a third embodiment, the organosilica material support may be a polymer of at least one monomer of Formula (I) and a monomer having at least one unit of Formula:

$Z^7Z^8Z^9Si—R^1—SiZ^7Z^8Z^9$ (III), where each $Z^7$ independently represents a hydroxyl group, a $C_1$-$C_4$ alkoxy group, or an oxygen atom bonded to a silicon atom of another comonomer; each of $Z^8$ and $Z^9$ independently represent a hydroxyl group, a $C_1$-$C_4$ alkoxy group, a $C_1$-$C_4$ alkyl group, or an oxygen bonded to a silicon atom of another monomer; and $R^1$ is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group.

In various aspects, each $Z^7$ can be a hydroxyl group or a $C_1$-$C_4$ alkoxy group, a $C_1$-$C_3$ alkoxy group, a $C_1$-$C_2$ alkoxy group, or methoxy, preferably a hydroxyl group, or a $C_1$-$C_2$ alkoxy group or oxygen atom bonded to a silicon atom of another comonomer. Each $Z^8$ and $Z^9$ can independently be a hydroxyl group a $C_1$-$C_4$ alkoxy group, a $C_1$-$C_3$ alkoxy group, a $C_1$-$C_2$ alkoxy group, or methoxy, a $C_1$-$C_4$ alkyl group, a $C_1$-$C_3$ alkyl group, a $C_1$-$C_2$ alkyl group, or methyl. Alternately, each $Z^8$ and $Z^9$ independently can be an oxygen atom bonded to a silicon atom of another comonomer. Each $Z^7$ can be a hydroxyl group, a $C_1$-$C_2$ alkoxy group, or an oxygen atom bonded to a silicon atom of another comonomer; and $Z^8$ and $Z^9$ each independently can be a hydroxyl group, a $C_1$-$C_2$ alkoxy group, a $C_1$-$C_2$ alkyl group, or an oxygen atom bonded to a silicon atom of another comonomer. When present with Formula (I), each $Z^7$ can be a hydroxyl group, ethoxy, methoxy or an oxygen atom bonded to a silicon atom of another comonomer; and each $Z^8$ and $Z^9$ independently can be a hydroxyl group, ethoxy, methyl, or an oxygen atom bonded to a silicon atom of another comonomer.

Each $R^1$ can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or $CH_2$.

Each $R^1$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

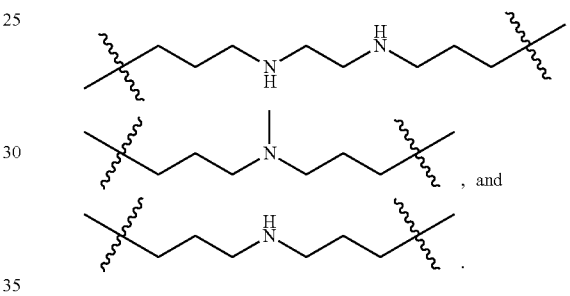

Each $Z^7$ can be a hydroxyl group, a $C_1$-$C_2$ alkoxy group, or an oxygen atom bonded to a silicon atom of another comonomer; each $Z^8$ and $Z^9$ independently can be a hydroxyl group, a $C_1$-$C_2$ alkoxy group, a $C_1$-$C_2$ alkyl group, or an oxygen atom bonded to a silicon atom of another comonomer; and $R^1$ can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Each $R^1$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Each $R^1$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Each $Z^7$ can be a hydroxyl group, ethoxy, methoxy or an oxygen atom bonded to a silicon atom of another comonomer; each Z8 and Z9 independently can be a hydroxyl group, ethoxy, methoxy, methyl, or an oxygen atom bonded to a silicon atom of another comonomer; and $R^1$ can be selected from the group consisting of —$CH_2$—, —$CH_2CH_2$—, —HC=CH—,

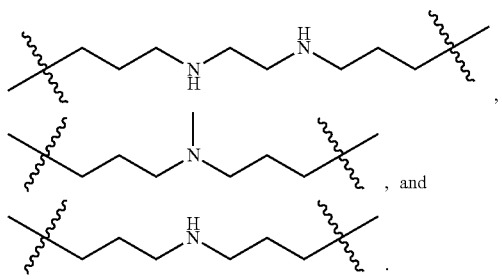

, and

Each $Z^7$ can be a hydroxyl group, or an oxygen atom bonded to a silicon atom of another comonomer; each $Z^8$ and $Z^9$ independently can be a hydroxyl group, methyl, or an oxygen atom bonded to a silicon atom of another comonomer; and $R^1$ can be selected from the group consisting of —$CH_2$—, —$CH_2CH_2$—, —HC=CH—,

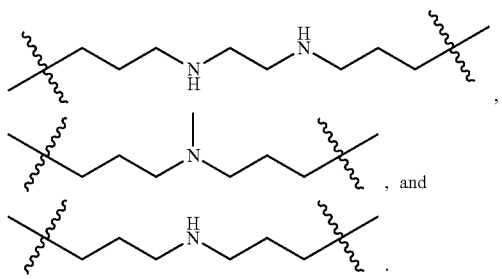

, and

In a particular embodiment, each $Z^7$ can be a hydroxyl group, ethoxy or an oxygen atom bonded to a silicon atom of another comonomer; each $Z^8$ can be a hydroxyl group, ethoxy, and an oxygen atom bonded to a silicon atom of another monomer; each $Z^9$ can be methyl; and $R^1$ can be —$CH_2CH_2$—.

In another particular embodiment, each $Z^7$ can be a hydroxyl group, ethoxy or an oxygen atom bonded to a silicon atom of another comonomer; each $Z^8$ and $Z^9$ independently can be selected from the group consisting of a hydroxyl group, ethoxy, and an oxygen atom bonded to a silicon atom of another monomer; and $R^1$ can be —$CH_2$— or —HC=CH—.

In another particular embodiment, each $Z^7$ can be a hydroxyl group, ethoxy or an oxygen atom bonded to a silicon atom of another comonomer; each $Z^8$ can be a hydroxyl group, ethoxy, and an oxygen atom bonded to a silicon atom of another monomer; each $Z^9$ can be methyl; and $R^1$ can be

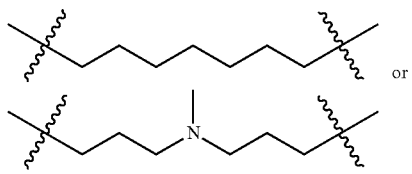

or

Monomers of Formula (IV)

In a fourth embodiment, the organosilica material support may be a polymer of at least one monomer of Formula (I) and a monomer having at least one trivalent metal oxide monomer of Formula $M^1(OZ^{10})_3$ (IV), where $M^1$ represents a Group 13 metal (preferably B, Al, Ga, In, or Tl, preferably B, Al or Ga, preferably Al) and $Z^{10}$ represents a hydrogen atom, a $C_1$-$C_6$ alkyl (preferably methyl, ethyl, propyl, butyl, pentyl or hexyl) or a bond to a silicon atom of another monomer.

Each $M^1$ can be B, Al, Ga, In Tl, or Uut. In particular, $M^1$ can be Al or B. Preferably $M^1$ can be Al or B and $Z^{10}$ can be a hydrogen atom, methyl, ethyl, propyl or butyl.

Each $Z^{10}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, or methyl. In particular, $Z^{10}$ can be methyl, ethyl, propyl or butyl.

When present with Formula (I), each $Z^1$ and $Z^2$ each independently can be can be a hydrogen atom, a $C_1$-$C_2$ alkyl group (methyl or ethyl), or a bond to a silicon atom of another monomer; each $M^1$ can be Al or B; and each $Z^{10}$ can be a hydrogen atom, methyl, ethyl, propyl, butyl or a bond to a silicon atom of another monomer.

Monomers of Formula (V)

In a fifth embodiment, the organosilica material support may be a polymer of at least one monomer of Formula (I) and a monomer having at least one trivalent metal oxide monomer of Formula $(Z^{11}O)_2M^2$-O—$Si(OZ^{12})_3$ (V), wherein $M^2$ represents a Group 13 metal (preferably B, Al, Ga, In, or Tl, preferably B, Al or Ga, preferably Al) and $Z^{11}$ and $Z^{12}$ each independently represent a hydrogen atom, a $C_1$-$C_6$ alkyl group (such as methyl, ethyl, propyl, butyl, pentyl or hexyl) or a bond to a silicon atom of another monomer.

Each $M^2$ can be B, Al, Ga, In Tl, or Uut. In particular, each $M^2$ can be Al or B. Preferably each $M^2$ can be Al or B and each $Z^{11}$ and $Z^{12}$ are a hydrogen atom.

Each $Z^{11}$ and/or $Z^{12}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, or methyl. In particular, each $Z^{11}$ and/or $Z^{12}$ can be methyl, ethyl, propyl or butyl.

In a particular embodiment, each $M^2$ can be Al; and $Z^{11}$ and/or $Z^{12}$ each independently can be a hydrogen atom, methyl, ethyl, propyl, butyl, or a bond to a silicon atom of another monomer.

Monomers of Formula (VI)

In a sixth embodiment, the organosilica material support may be a polymer of at least one cyclic polyurea monomer. The organosilica material may be a polymer formed of multiple distinct monomers, including a monomer of Formula I in combination with one or more cyclic polyurea monomers. A suitable cyclic polyurea monomer of Formula

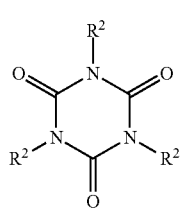

(VI)

where $R^2$ is a $Z^{13}OZ^{14}Z^{15}SiZ^{16}$ group, wherein each $Z^{13}$ represents a hydrogen atom, a $C_1$-$C_4$ alkyl group, or a bond to a silicon atom of another monomer unit; each $Z^{14}$ and $Z^{15}$ independently represents a hydroxyl group, a $C_1$-$C_4$ alkyl group, a $C_1$-$C_4$ alkoxy group or an oxygen atom bonded to a silicon atom of another monomer unit; and each $Z^{16}$ represents a $C_1$-$C_8$ alkylene group bonded to a nitrogen atom of the cyclic polyurea.

In certain other aspects, the organosilica material support may be a polymer formed of monomers of Formula VI, with or without any other monomers, including those of Formula I.

In various embodiments, each $Z^{13}$ can be methyl, ethyl, propyl, or butyl, preferably methyl or ethyl. Alternately, each $Z^{14}$ and $Z^{15}$ independently can be a hydroxyl group. Each $Z^{14}$ and $Z^{15}$ independently can be methyl, ethyl, propyl, or butyl, preferably methyl or ethyl. Each $Z^{14}$ and $Z^{15}$ independently can be a $C_1$-$C_4$ alkoxy group, a $C_1$-$C_3$ alkoxy group, a $C_1$-$C_2$ alkoxy group or methoxy.

Each $Z^{16}$ can be a $C_1$-$C_7$ alkylene group bonded to a nitrogen atom of the cyclic polyurea, a $C_1$-$C_7$ alkylene group bonded to a nitrogen atom of the cyclic polyurea, a $C_1$-$C_6$ alkylene group bonded to a nitrogen atom of the cyclic polyurea, a $C_1$-$C_4$ alkylene group bonded to a nitrogen atom of the cyclic polyurea, a $C_1$-$C_3$ alkylene group bonded to a nitrogen atom of the cyclic polyurea, a $C_1$-$C_2$ alkylene group bonded to a nitrogen atom of the cyclic polyurea, or —$CH_2$— bonded to a nitrogen atom of the cyclic polyurea.

Each $Z^{13}$ can be a hydrogen atom, a $C_1$-$C_2$ alkyl group or a bond to a silicon atom of another monomer; each $Z^{14}$ and $Z^{15}$ independently can be a hydroxyl group, a $C_1$-$C_2$ alkyl group, a $C_1$-$C_2$ alkoxy group, or an oxygen atom bonded to a silicon atom of another monomer unit; and $Z^{16}$ can be a $C_1$-$C_4$ alkylene group bonded to a nitrogen atom of the cyclic polyurea. Each $Z^{13}$ can be a hydrogen atom, methyl, or a bond to a silicon atom of another monomer; each $Z^{14}$ and $Z^{15}$ independently can be a hydroxyl group, methoxy or an oxygen atom bonded to a silicon atom of another monomer unit; and each $Z^{16}$ can be —$CH_2CH_2CH_2$— bonded to a nitrogen atom of the cyclic polyurea.

Organosilica Material Characterization

In certain aspects, the invention relates to organosilica material supports that may be a polymer formed from a reaction of any of the monomers of Formulas (I)-(VI), although in certain alternative variations, the organosilica materials are not limited to only these monomers. Furthermore, in certain embodiments, the organosilica material support may be a polymer formed of multiple distinct monomers, including any combinations of monomers of Formula (I) with one or more monomers of Formulas (II)-(VI). As noted above, in certain alternative embodiments, the organosilica material support may be a polymer formed of one or more monomers of Formula (VI), with or without other monomers of Formulas (I)-(V).

The inventive technology thus uses the monomer building blocks described above to form an organosilane having a high surface area and high porosity without use of any structure directing agent (SDA), porogen. However, in certain aspects, the pores in the organosilane materials of the invention are not arranged in an ordered structure as they would be if formed with a structure directing agent (SDA). Conventional periodic mesoporous organosilicas (PMO) materials have highly ordered pore structures that occur by use of SDAs (typically surfactants) during reaction formations. In contrast, in certain aspects, the organosilica material support of the present disclosure may be formed without use of any SDAs or porogens as a template, while still exhibiting relatively ordered pore structures and desirably high surface area and porosity levels.

In various aspects, the organosilica materials described herein can be characterized as described in the following sections. Further description and characterization of suitable organosilica materials for use as catalyst supports can be found in "CO-FILED CASES" which are defined to be: 1) U.S. Ser. No. 14/966,001; filed Dec. 11, 2015; 2) U.S. Ser. No. 14/965,992; filed Dec. 11, 2015; 3) U.S. Ser. No. 14/965,984; filed Dec. 11, 2015; 4) U.S. Ser. No. 14/966,383; filed Dec. 11, 2015; 5) U.S. Ser. No. 14/966,015; filed Dec. 11, 2015; 6) U.S. Ser. No. 14/966,284; filed Dec. 11, 2015, which are incorporated herein by reference in their entireties.

X-Ray Diffraction Peaks

The organosilica material supports described herein can exhibit powder X-ray diffraction patterns with one broad peak between about 1 and about 4 degrees 2θ, particularly one peak between about 1 and about 3 degrees 2θ, or particularly one peak between about 1 and about 2 degrees 2θ. The organosilica materials can exhibit substantially no peaks in the range of about 0.5 to about 10 degrees 2θ, or about 0.5 to about 70 degrees 2θ, or about 2 to about 10 degrees 2θ, or about 2 to about 70 degrees 2θ, or about 3 to about 10 degrees 2θ, or about 3 to about 70 degrees 2θ.

Silanol Content

The organosilica material supports can have a silanol content that varies within wide limits, depending on the composition of the synthesis solution. The silanol content can conveniently be determined by solid state silicon NMR, more specifically by using solid state $^{29}$Si or $^1$H NMR.

In various aspects, the organosilica material supports can have a silanol content of greater than about 5%. In certain embodiments, the silanol content can be greater than about 30% or greater than about 41%. The organosilica material supports may have a silanol content of about 5% to about 80%, or about 5% to about 50%, or about 5% to about 25%, or about 5% to about 10%, or about 10% to about 50%, or about 10% to about 20%, or about 20% to about 30%, or about 30% to about 50%.

Pore Size

The organosilica material supports described herein are advantageously in a mesoporous form. As indicated previously, the term mesoporous refers to solid materials having pores with a diameter within the range of from greater than or equal to about 2 nm to less than or equal to about 50 nm. The average pore diameter of the organosilica material can be determined, for example, using nitrogen adsorption-desorption isotherm techniques within the expertise of one of skill in the art, such as the BET (Brunauer Emmet Teller) method. Pore size can be measured by the Brunauer-Emmett-Teller (BET) method using adsorption-desorption of nitrogen (temperature of liquid nitrogen, 77 K) with a Micromeritics Tristar II 3020 instrument after degassing of the powders for 4 hrs. at 350° C. Typically, the samples are pre-treated with 120° C./vacuum/4 hours before the BET analysis is conducted. More information regarding the method can be found, for example, in S. Lowell et al., "Characterization of Porous Solids and Powders: Surface Area, Pore Size and Density," Springer (2004).

The organosilica material supports can have an average pore diameter of about 0.2 nm to less than about 2.0 nm in certain variations. The organosilica material supports can advantageously have an average pore diameter within the mesopore range of about 2.0 nm to about 50 nm. The organosilica material supports can have an average pore diameter of 0.2 nm to about 50 nm, or about 1.0 nm to about 50 nm, or in the mesopore range of about 2.0 nm to about 50 nm, about 2.0 nm to about 40 nm, about 2.0 nm to about 30 nm, about 2.0 nm to about 20 nm, about 2.0 nm to about 10 nm, about 2.0 nm to about 5.0 nm, and about 2.0 nm to about 4.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from N2 adsorption isotherm experiments. In such circumstances, without being bound by theory, the hysteresis can result from the lack of regularity in the pore shapes/sizes and/or from bottleneck constrictions in such irregular pores.

Surface Area

The surface area of the organosilica material supports can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method. Surface area determined by the BET method uses adsorption-desorption of nitrogen (temperature of liquid nitrogen, 77 K) with a Micromeritics Tristar II 3020 instrument after degassing of the powders for 4 hrs. at 350° C. Typically, the samples are pre-treated with 120° C./vacuum/4 hours before the BET analysis is conducted. More information regarding the method can be found, for example, in S. Lowell et al., "Characterization of Porous Solids and Powders: Surface Area, Pore Size and Density," Springer (2004).

In various embodiments, the organosilica material supports can have a total (e.g., BET) surface area greater than or equal to 2 $m^2/g$ to less than or equal to about 2,500 $m^2/g$, about 50 $m^2/g$ to about 2,500 $m^2/g$, about 100 $m^2/g$ to about 2,500 $m^2/g$, about 200 $m^2/g$ to about 2,500 $m^2/g$, about 300 $m^2/g$ to about 2,500 $m^2/g$, or about 400 $m^2/g$ to about 2,500 $m^2$g.

Pore Volume

The pore volume of the organosilica material supports described herein can be determined, for example, using nitrogen adsorption-desorption isotherm techniques within the expertise of one of skill in the art, such as the total (Brunauer Emmet Teller) method described above. The organosilica material supports can have a pore volume of about 0.1 $cm^3/g$ to about 10.0 $cm^3/g$, about 0.1 $cm^3/g$ to about 5.0 $cm^3/g$, about 0.1 $cm^3/g$ to about 2.0 $cm^3/g$, about 0.1 $cm^3/g$ to about 1.0 $cm^3/g$, or about 0.1 $cm^3/g$ to about 0.5 $cm^3/g$.

In a particular embodiment, the organosilica material supports can have a pore volume of about 0.1 $cm^3/g$ to about 5.0 $cm^3/g$, particularly about 0.1 $cm^3/g$ to about 3.0 $cm^3/g$, particularly about 0.2 $cm^3/g$ to about 2.5 $cm^3/g$, or particularly about 0.2 $cm^3/g$ to about 1.5 $cm^3/g$.

Particle Size

The organosilica material supports can have an average particle size in the range of from greater than or equal to about 5 µm to about 500 µm. Average particle size, also referred to as "particle size," or "particle diameter" is determined using a Mastersizer™ 3000 (range of 1 to 3500 µm) available from Malvern Instruments, Ltd. Worcestershire, England. Particle size distribution via laser sizing can also be a method of measuring ranges of average particles sizes and particle dispersion.

Dried Particles

The organosilica material support material may be dry, that is, free of absorbed water. Drying of the organosilica material can be effected by heating or calcining at a range of greater than or equal to about 100° C. to less than or equal to about 1000° C. for a time of about 1 minute to about 100 hours. The calcined material preferably has at least some reactive oxygen containing groups, such as hydroxyl (OH) groups.

In another particular embodiment, an organosilica material as described herein i) has an X Ray Diffraction Spectrum exhibiting substantially no peaks above 4 degrees 2θ; and/or ii) is made using substantially no added structure directing agent or porogen.

Methods of Making Organosilica Material Supports

In another embodiment, methods of producing the organosilica material supports described herein are provided. The method comprises:

providing an aqueous mixture that contains essentially no structure directing agent and/or porogen;

adding at least one compound of Formula $[R^3R^4SiCH_2]_3$ (Ia) into the aqueous mixture to form a solution, wherein $R^3$ can be a $C_1$-$C_4$ alkoxy group and $R^4$ can be a $C_1$-$C_4$ alkoxy group or a $C_1$-$C_4$ alkyl group;

aging the solution to produce a pre-product (for example, a gel); and drying the pre-product to obtain an organosilica material which is a polymer comprising at least one monomer of Formula (I) as described herein.

Aqueous Mixture

The organosilica material supports described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

Structure Directing Agent

Examples of a structure directing agent can include, but are not limited to, non-ionic surfactants (e.g., nonionic polyoxyethylene alkyl ethers), ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. The surface directing agent can comprise or be a poloxamer (e.g., block copolymers of ethylene oxide and propylene oxide), a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Each porogens can be thermoplastic homopolymers and random (as opposed to block) copolymers. The porogen can be a solvent. As noted above, further examples of various surface directing agents and porogens are included in CO-FILED CASES, as defined above.

Base/Acid

In various embodiments, the aqueous mixture used in methods provided herein can comprise a base and/or an acid. In certain embodiments where the aqueous mixture comprises a base, the aqueous mixture can have a pH from about 8 to about 15, from about 8 to about 14, from about 9 to about 14, from about 10 to about 14, from about 10 to about 13, or from about 11 to about 13.

In a particular embodiment comprising a base, the pH can be from about 9 to about 15 or from about 9 to about 14. Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide.

In certain embodiments where the aqueous mixture comprises an acid, the aqueous mixture can have a pH from about 0.01 to about 6.0, about 0.2 to about 5.0, from about 0.5 to about 4.0, from about 1.0 to about 4, or from about 2 to about 4. In a particular embodiment comprising an acid, the pH can be from about 0.01 to about 6.0, about 0.2 to about 6.0, about 0.2 to about 5.0 or about 0.2 to about 4.5.

Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

In various aspects, adjusting the pH of the aqueous mixture can affect the total surface area, microporous surface area and pore volume of the organosilica material support made. Thus, the porosity of the organosilica material may be adjusted by adjusting the pH of the aqueous mixture.

For example, when the aqueous mixture is basic and has a pH between about 8 to about 14, in particular about 9 to about 14, the organosilica material support made may have one or more of the following characteristics: a) a total surface area of about 200 $m^2/g$ to about 1800 $m^2/g$, particularly about 300 $m^2/g$ to about 1700 $m^2/g$, and particularly about 400 $m^2/g$ to about 1700 $m^2/g$; b) a microporous surface area of about 0 $m^2/g$ to about 700 $m^2/g$, and particularly about 0 $m^2/g$ to about 700 $m^2/g$; and c) a pore volume of about 0.2 $cm^3/g$ to about 3 $cm^3/g$, and particularly of about 0.8 $cm^3/g$ to about 1.4 $cm^3/g$.

When the aqueous mixture is acidic and has a pH between about 0.1 to about 7, particularly about 0.1 to about 5, particularly about 0.1 to about 4.5, the organosilica material made may have one or more of the following characteristics: a) a total surface area of about 100 $m^2/g$ to about 1500 $m^2/g$, particularly about 100 $m^2/g$ to about 900 $m^2/g$, and particularly about 200 $m^2/g$ to about 900 $m^2/g$; b) a microporous surface area of about 100 $m^2/g$ to about 600 $m^2/g$, and particularly about 0 $m^2/g$ to about 500 $m^2/g$; and c) a pore volume of about 0.1 $cm^3/g$ to about 1.2 $cm^3/g$, and particularly of about 0.1 $cm^3/g$ to about 0.6 $cm^3/g$.

Thus, the total surface area of an organosilica material support made with a basic aqueous mixture may increase when compared to an organosilica material made with an acidic aqueous mixture. Further, the pore volume of an organosilica material support made with a basic aqueous mixture may increase when compared to an organosilica material made with an acidic aqueous mixture. However, the microporous surface area of an organosilica material support made with a basic aqueous mixture may decrease when compared to an organosilica material made with an acidic aqueous mixture.

Compounds of Formula Ia

The methods provided herein comprise the step of adding at least one compound of Formula $[R^3R^4SiCH_2]_3$ (Ia) into the aqueous mixture to form a solution to obtain an organosilica material support which is a homopolymer or copolymer comprising at least one unit of Formula (I), wherein $R^3$ can be a $C_1$-$C_4$ alkoxy group and $R^4$ can be a $C_1$-$C_4$ alkoxy group or a $C_1$-$C_4$ alkyl group.

In one embodiment, $R^3$ can comprise a $C_1$-$C_3$ alkoxy or methoxy or ethoxy. Each $R^3$ can be a $C_1$-$C_2$ alkoxy group and $R^4$ can be a $C_1$-$C_2$ alkoxy group or a $C_1$-$C_2$ alkyl group. Each $R^3$ can be methoxy or ethoxy and $R^4$ can be methyl or ethyl.

Each $R^4$ can comprise a $C_1$-$C_4$ alkoxy, a $C_1$-$C_3$ alkoxy or methoxy or ethoxy. Each $R^4$ can comprise methyl, ethyl or propyl, such as a methyl or ethyl.

In a particular embodiment, $R^3$ and $R^4$ can be ethoxy, such that the compound corresponding to Formula (Ia) can be 1,1,3,3,5,5-hexaethoxy-1,3,5-trisilacyclohexane, ($[(EtO)_2SiCH_2]_3$). In a particular embodiment, $R^3$ can be ethoxy and $R^4$ can be methyl, such that compound corresponding to Formula (Ia) can be 1,3,5-trimethyl-1,3,5-triethoxy-1,3,5-trisilacyclohexane, ($[EtOCH_3SiCH_2]_3$).

Compounds of Formula IIa

In additional embodiments, the methods provided herein can further comprise adding to the aqueous solution a compound of Formula $R^5OR^6R^7R^8Si$ (IIa) to obtain an organosilica material support which is a copolymer comprising at least one unit of Formula (I), at least one unit of Formula (II) and optionally at least one unit of Formulas (III)-(VI) as described herein. $R^5$ of Formula (IIa) can be a $C_1$-$C_6$ alkyl group, and $R^6$, $R^7$ and $R^8$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

In other particular embodiments, compounds corresponding to Formula (IIa) can be tetraethyl orthosilicate (TEOS) (($(EtO)_4Si$), methyltriethoxysilane (MTES) (($(EtO)_3CH_3Si$), (3-aminopropyl)triethoxysilane ($H_2N(CH_2)_3(EtO)_3Si$), (N,N-dimethylaminopropyl)trimethoxysilane ((($(CH_3)_2N(CH_2)_3)(MeO)_3Si$), (N-(2-aminoethyl)-3-aminopropyltriethoxysilane (($H_2N(CH_2)_2NH(CH_2)_3)(EtO)_2Si$), 4-methyl-1-(3-triethoxysilylpropyl)-piperazine, 4-(2-(triethoxysilyl)ethyl)pyridine, and/or 1-(3-(triethoxysilyl)propyl)-4,5-dihydro-1H-imidazole.

In another particular embodiment, a compound of Formula (Ia) can be 1,1,3,3,5,5-hexaethoxy-1,3,5-trisilacyclohexane ($[(EtO)_2SiCH_2]_3$ can be combined with any of the compounds of Formula (IIa) described above. In certain other embodiments, these compounds can be further combined with a trivalent metal oxide source, such as aluminum tri-sec-butoxide.

Compounds of Formula IIIa

In additional embodiments, the methods provided herein can further comprise adding to the aqueous solution a compound of Formula $Z^{17}Z^{18}Z^{19}Si$—$R^9$—$Si\ Z^{17}Z^{18}Z^{19}$ (IIIa) to obtain an organosilica material support which is a copolymer comprising at least one unit Formula (I) as described herein, at least one unit Formula (III) as described herein, and optionally at least one unit of Formulas (II) or (IV)-(VI) as described herein. In Formula (IIIa), each $Z^{17}$ can independently be a $C_1$-$C_4$ alkoxy group; each $Z^{18}$ and $Z^{19}$ independently can be a $C_1$-$C_4$ alkoxy group or a $C_1$-$C_4$ alkyl group; and $R^9$ can be selected from the group consisting a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

In other particular embodiments, compounds corresponding to Formula (IIIa) can be 1,2-bis(methyldiethoxysilyl)ethane ($CH_3(EtO)_2Si$—$CH_2CH_2$—$Si(EtO)_2CH_3$), 1,2-bis(triethoxysilyl)ethylene (($(EtO)_3Si$—$HC$=$CH$—$Si(EtO)_3$), N,N'-bis[(3-trimethoxysilyl)propyl]ethylenediamine, and/or bis[(methyldiethoxysilyl)propyl]amine, bis[(methyldimethoxysilyl)propyl]-N-methylamine.

In a particular embodiment, compounds corresponding to Formula In another particular embodiment, a compound of Formula (Ia) can be 1,1,3,3,5,5-hexaethoxy-1,3,5-trisilacyclohexane ($[(EtO)_2SiCH_2]_3$ can be combined with any of the compounds of Formula (IIIa) described above. In certain other embodiments, these compounds can be further combined with a trivalent metal oxide source, such as aluminum tri-sec-butoxide.

Compounds of Formula IVa

In additional embodiments, the methods provided herein can comprise adding to the aqueous solution a source of a trivalent metal oxide to obtain an organosilica material support which is a copolymer comprising at least one unit Formula (I) as described herein, at least one unit Formula (IV) as described herein, and optionally at least one unit of Formulas (II), (III), (V) or (VI) as described herein.

In various aspects, the source of trivalent metal oxide may be a compound of formula $M^3(OZ^{20})_3$ (IVa), wherein $M^3$ can be a Group 13 metal and $Z^{20}$ can be a $C_1$-$C_6$ alkyl group. In one embodiment, $M^3$ can be B, Al, Ga, In, Il, or Uut. In particular, $M^3$ can be Al or B. Each $Z^{20}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{15}$ can be methyl, ethyl, propyl or butyl.

In other particular embodiments, compounds corresponding to Formula (IVa) can be aluminum trimethoxide, aluminum triethoxide, aluminum isopropoxide and/or aluminum tri-sec-butoxide.

Each sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAl_2$, boron nitride, $B_2O_3$ and/or $H_3BO_3$. The source of a trivalent metal oxide may be a source of a compound of Formula (IV).

Compounds of Formula Va

In yet other additional embodiments, the methods provided herein can comprise adding to the aqueous solution another source of a trivalent metal oxide to obtain an organosilica material support which is a copolymer comprising at least one unit Formula (I) as described herein, at least one unit Formula (V) as described herein, and optionally at least one unit of Formulas (II), (III), (IV) or (VI) as described herein.

The source of trivalent metal oxide may be a compound of Formula $(Z^{21}O)_2M^5$—$O$—$Si(OZ^{22})_3$ (Va), wherein $M^5$ can be a Group 13 metal and $Z^{21}$ and $Z^{22}$ each independently can be a $C_1$-$C_6$ alkyl group. In one embodiment, $M^2$ can be B, Al, Ga, In, Il, or Uut. In particular, $M^5$ can be Al or B. Each $Z^{21}$ and $Z^{22}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{21}$ and $Z^{22}$ each independently can be methyl, ethyl, propyl or butyl.

As noted above, sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, $Al_2O_3$, aluminum halides (e.g., $AlCl_3$), $NaAlO_2$, boron nitride, $B_2O_3$ and/or $H_3BO_3$. The source of a trivalent metal oxide may be a source of a compound of Formula (Va).

Compounds of Formula VIa

The methods provided herein comprise the step of adding at least one cyclic compound of Formula

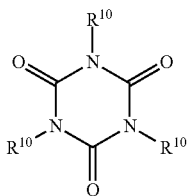

(VIa)

into the aqueous mixture to form a solution to obtain an organosilica material support which is a copolymer comprising at least one unit Formula (I) as described herein, at least one unit Formula (VI) as described herein, and optionally at least one unit of Formulas (II)-(V) as described herein, wherein each $R^{10}$ independently can be a $X^1OX^2X^3SiX^4$ group, wherein each $X^1$ can independently be a $C_1$-$C_4$ alkyl group; each $X^2$ and $X^3$ independently can be a $C_1$-$C_4$ alkyl group or a $C_1$-$C_4$ alkoxy group; and each $X^4$ can be a $C_1$-$C_8$ alkylene group bonded to a nitrogen atom of the cyclic compound.

In another particular embodiment, a compound of Formula (IIa) can be tetraethyl orthosilicate (TEOS) ($(EtO)_4Si$) and a compound of Formula (VIa) can be tris(3-trimethoxysilylpropyl)isocyanurate.

In another particular embodiment, a compound of Formula (Ia) can be 1,1,3,3,5,5-hexaethoxy-1,3,5-trisilacyclohexane, ($[(EtO)_2SiCH_2]_3$) and a compound of Formula (VIa) can be tris(3-trimethoxysilylpropyl)isocyanurate.

Metal Chelate Sources

In additional embodiments, the methods provided herein can further comprise adding to the aqueous solution a source of metal chelate compounds. Examples of metal chelate compounds, are disclosed in U.S. Ser. No. 14/966,001; filed Dec. 11, 2015. Of these, the chelate compounds of titanium or aluminum can be of note, of which the chelate compounds of titanium can be particularly of note. These metal chelate compounds may be used either singly or in combination.

Molar Ratio

In the methods described herein, in certain variations, where a plurality of monomers is selected to form the organosilica support polymer, molar ratios of Formula (Ia): Formula (Ia), Formula (Ia): Formula (IIa), Formula (Ia): Formula (IIIa) Formula (Ia): Formula (IVa), Formula (Ia): Formula (Va), or Formula (Ia): Formula (VIa) may optionally be about 99:1 to about 1:99, about 75:1 to about 1:75, about 50:1 to about 1:50, about 25:1 to about 1:25, about 15:1 to about 1:15, or about 10:1 to about 1:10. For example, a molar ratio of Formula (Ia):Formula (Ia) can be about 3:2. A molar ratio of Formula (Ia):Formula (II) can be about 2:3, about 4:3, about 4:1 or about 3:2. A molar ratio of Formula (Ia):Formula (III) can be about 2:3, and about 4:1. A molar ratio of Formula (III): Formula (II) can be about 5:2, about 1:1, about 1:2 or about 2:3. A molar ratio of Formula (Ia): Formula (IV), Formula (Ia): Formula (V), or Formula (Ia): Formula (VI) can be about 15:1 or about 5:1.

Aging the Solution

The solution formed in the methods described herein can be aged for at least about 4 hours. The solution formed in the methods described herein can be aged for about 4 hours to about 144 hours (6 days), or about 96 hours (4 days) to about 120 hours (5 days), or about 120 hours (5 days) to about 144 hours (6 days). The solution formed in the method can be aged at temperature of about 10° C. to about 300° C., about 50° C. to about 300° C., about 100° C. to about 300° C., 130° C. to about 250° C., about 130° C. to about 200° C., about 130° C. to about 150° C., or about 130° C. to about 140° C. In various aspects, adjusting the aging time and/or aging temperature of the solution formed in the methods described herein can affect the total surface area, microporous surface area, pore volume, pore radius and pore diameter of the organosilica material made. Thus, the porosity of the organosilica material may be adjusted by adjusting aging time and/or temperature.

For example, when the solution is aged for about 1 hour to about 7 hours (e.g., 1, 2, 3, 4, 5, 6 hours) at a temperature of about 80° C. to about 100° C. (e.g., 80° C., 85° C., 90° C., 95° C., etc.), the organosilica material support may have one or more of the following: a) a total surface area of about 200 m²/g to about 1400 m²/g, particularly about 400 m2/g to about 1300 m²/g, and particularly about 400 m²/g to about 1200 m²/g; b) a microporous surface area of about 200 m²/g to about 600 m²/g, particularly about 200 m²/g to about 500 m²/g; c) a pore volume of about 0.2 cm³/g to about 1.0 cm³/g, particularly about 0.2 cm³/g to about 0.8 cm³/g; and d) an average pore radius of about 0.5 nm to about 2.0 nm, particularly about 0.5 nm to about 2.0 nm, and particularly about 1.0 nm to about 1.5 nm.

When the solution is aged for greater than about 7 hours to about 150 hours (e.g., 23, 48, 72, 144 hours) at a temperature of about 80° C. to about 100° C. (e.g., 80° C., 85° C., 90° C., 95° C., etc.), the organosilica material support may have one or more of the following: a) a total surface area of about 600 m²/g to about 1400 m²/g, particularly about 800 m²/g to about 1400 m²/g, and particularly about 800 m²/g to about 1200 m²/g; b) substantially no microporous surface area; c) a pore volume of about 0.8 cm³/g to about 1.4 cm³/g, particularly about 0.9 cm³/g to about 1.4 cm³/g; and d) an average pore radius of about 1.0 nm to about 4.0 nm, particularly about 1.0 nm to about 4.0 nm.

When the solution is aged for about 1 hour to about 7 hours (e.g., 1, 2, 3, 4, 5, 6 hours) at a temperature of about 110° C. to about 130° C. (e.g., 110° C., 115° C., 120° C., 125° C., etc.), the organosilica material support may have one or more of the following: a) a pore volume of about 1.0 cm³/g to about 1.8 cm³/g, particularly about 1.2 cm³/g to about 1.8 cm³/g, particularly about 1.4 cm³/g to about 1.7 cm³/g; and b) an average pore diameter of about 2.0 nm to about 8.0 nm, particularly 4.0 nm to about 6.0 nm.

When the solution is aged for greater than about 7 hours to about 150 hours (e.g., 23, 48, 72, 144 hours) at a temperature of about 110° C. to about 130° C. (e.g., 110° C., 115° C., 120° C., 125° C., etc.), the organosilica material support may have one or more of the following: a) a pore volume of about 1.0 cm³/g to about 1.8 cm³/g, particularly about 1.2 cm³/g to about 1.8 cm³/g; and b) an average pore diameter of about 8.0 nm to about 16.0 nm, particularly about 10.0 nm to about 16.0 nm, particularly about 10.0 nm to about 14.0 nm.

Thus, at shorter aging times (e.g., 7, 6, 5, 4 hours, etc.) the surface area of an organosilica material made is microporous and mesoporous, but as aging time increase, the surface area transitions to primarily mesoporous. Further, as aging time increases, pore volume, average pore radius and average pore diameter increases. Increasing aging temperature along with aging time, accelerates the above-described surface area transition and increase in pore volume, average pore radius and average pore diameter.

Drying the Pre-Product

The methods described herein comprise drying the pre-product to produce an organosilica material support. In certain variations, the pre-product may be a gel.

In some embodiments, the pre-product (e.g., gel) formed in the method can be dried at a temperature of about 50° C. to about 600° C. In a particular embodiment, the pre-product (e.g., gel) formed in the method can be dried at temperature from about 70° C. to about 200° C.

The pre-product (e.g., gel) formed in the method can be dried in a $N_2$ and/or air atmosphere.

Additional Organosilica Support Processing Steps

The organosilica material support material is dry, that is, free of absorbed water. Drying of the support material can be effected by heating or calcining at about 100° C. to about 1000° C., preferably at least about 600° C. When the support material is an organosilica, it is typically heated to about 200° C. to about 850° C.; and for a time of about 1 minute to about 100 hours, from about 12 hours to about 72 hours, or from about 24 hours to about 60 hours.

In some embodiments, as noted above, the method can further comprise calcining the organosilica material to obtain a silica material. The calcining can be performed in air or an inert gas, such as nitrogen or air enriched in nitrogen. Calcining can take place at a temperature of at least about 175° C., for example, calcining can be performed at a temperature of about 175° C. to about 650° C.

The calcined support material comprising the organosilica material support may then be contacted with at least one polymerization catalyst comprising at least one metallocene compound and an activator.

Introducing Additional Catalyst Metals and Activators

In various embodiments, the organosilica material support can further comprise at least one catalyst metal incorporated within the pores of the organosilica material support, as will be described below. Exemplary catalyst metals can include, but are not limited to, a Group 6 element, a Group 8 element, a Group 9 element, a Group 10 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum.

The catalyst metal can be incorporated into the organosilica material by any convenient method, such as by impregnation, by ion exchange, or by complexation to surface sites. The catalyst metal so incorporated may be employed to promote any one of a number of catalytic transformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder. Suitable binders, include but are not limited to silica, alumina, zirconia, titania, silica-alumina, cerium oxide, magnesium oxide, or combinations thereof. Thus, in another embodiment, a catalyst material comprising the organosilica material described herein is provided.

In some embodiments, the organosilica material can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

The organosilica material can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Groups 1, 2, 6, 8-10 and/or 13 elements may be present on an exterior and/or interior surface of the organosilica material. For example, one or more of the Groups 1, 2 and/or 13 elements may be present in a first layer on the organosilica material and one or more of the Groups 6, 8, 9 and/or 10 elements may be present in a second layer, e.g., at least partially atop the Group 1, 2 and/or 13 elements. Each only one or more Groups 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like.

In certain embodiments, the support material, having reactive surface groups, typically hydroxyl groups, may be slurried in a non-polar solvent and the resulting slurry is contacted with a solution of a catalyst compound and optionally an activator. In certain variations, the catalyst compound comprises a metallocene compound, so that the solution comprises a metallocene compound. In some embodiments, the slurry of the support material is first contacted with the activator for a period of time in the range of from about 0.5 hours to about 24 hours, from about 2 hours to about 16 hours, or from about 4 hours to about 8 hours. The solution of the catalyst compound, e.g., metallocene compound, is then contacted with the isolated support/activator. In some embodiments, the supported catalyst system is generated in situ. In alternate embodiments, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated from greater than or equal to about 0° C. to less than or equal to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which the activator and the catalyst compound, e.g., metallocene compound, are at least partially soluble and which are liquid at reaction temperatures. Useful non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Organosilica Material Product-by-Process

Organosilica materials can be made from the methods described herein. In another particular embodiment, organosilica materials made from an aqueous mixture as described herein that contains essentially no structure directing agent or porogen as described herein, wherein the organosilica material may be a polymer comprising at least one unit of Formula (I) as described herein. In other aspects, organosilica materials made from an aqueous mixture as described herein that contains essentially no structure directing agent or porogen as described herein, wherein the organosilica material may be a polymer comprising at least Formula (VI) as described herein.

In yet another particular embodiment, organosilica materials made from an aqueous mixture as described herein that contains essentially no structure directing agent or porogen as described herein, wherein the organosilica material may be a copolymer of: a) at least one unit of Formula (I) as described herein; b) at least one unit of Formula (II) as described herein; c) at least one unit of Formula (III) as described herein; d) at least one unit of Formula (IV) as described herein; e) at least one unit of Formula (V) as described herein; and/or f) at least Formula (VI) as described herein.

The organosilica materials made from the methods described herein may exhibit an X Ray Diffraction (XRD) pattern as described herein, particularly with only one peak between about 1 and about 4 degrees 2θ. The organosilica materials may have an average pore diameter as described herein, particularly, between about 1.5 nm and about 20.0 nm.

In another particular embodiment, an organosilica material made from aqueous mixture as described herein that contains essentially no structure directing agent or porogen as described herein i) has an X Ray Diffraction Spectrum exhibiting substantially no peaks above 4 degrees 2θ; and/or ii) is made using substantially no added structure directing agent or porogen.

The organosilica materials can exhibit substantially no peaks in the range of about 0.5 to about 10 degrees 2θ, about 0.5 to about 12 degrees 2θ range, about 0.5 to about 15 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 70 degrees 2θ, about 3 to about 10 degrees 2θ, or about 3 to about 70 degrees 2θ.

In yet another variation, the organosilica material made from aqueous mixture as described herein that contains essentially no structure directing agent or porogen as described herein may have (i) an average pore diameter between about 1.5 nm and about 25.0 nm; (ii) a pore volume about 0.1 cm$^3$/g to about 10.0 cm$^3$/g; and/or (ii) a surface area of about 200 m$^2$/g to about 2,500 m$^2$/g.

Catalyst Compounds

In certain aspects, the one or more catalyst compounds may be one or more olefin polymerization catalyst compounds, preferably olefin coordination polymerization catalyst compounds. The catalyst compounds may be one or more metallocene catalyst compounds. Useful catalysts include compounds represented by the Formula $T_y Cp_m M^6 G_n X^5_q$ (VII), where Cp is a cyclopentadienyl group (such as cyclopentadiene, indene or fluorene) which may be substituted or unsubstituted, M$^6$ is a Group 4, 5 or 6 transition metal, for example titanium, zirconium, hafnium, vanadium, niobium, tantalum, chromium, molybdenum and tungsten, preferably Hf, Ti or Zr, G is a heteroatom group represented by the formula JR*$_z$ where J is a group 15 or 16 element, preferably N, P, O or S, and R* is a C$_1$ to C$_{20}$ hydrocarbyl group and z is 1 or 2, T is a bridging group, and y is 0 or 1, each X$^5$ is, independently, a leaving group, or two X$^5$ are joined and bound to the metal atom to form a metallocycle ring, or two X$^5$ are joined to form a chelating ligand, a diene ligand, or an alkylidene ligand; and m=1 or 2, n=0, 1, 2 or 3, q=0, 1, 2 or 3, and the sum of m+n+q is equal to the oxidation state of the transition metal (preferably 2, 3, 4, 5, or 6, preferably 4 or 5, preferably 4). In the present invention at least two metallocenes are present on the support where in the first metallocene m is 1, n is 1, and y is 1 and in the second metallocene n is 0 and in is 2, provided that when y=1 in the second metallocene compound, then at least one Cp is preferably not an indene group.

In a preferred embodiment of the invention, M$^6$ is a Group 4 transition metal (preferably Hf, Ti and/or Zr). In an embodiment when M$^6$ is Ti, then m is 1. In another embodiment when M$^6$ is Zr, then m is 2 or 3. In an embodiment when M$^6$ is Ti, then m is 1 and when M$^6$ is Zr, then m is 2. In a useful embodiment, two metallocenes are present and in the first metallocene M$^6$ is Ti and in the second metallocene M$^6$ is Hf or Zr.

Typically, each G is, independently, a heteroatom group represented by the formula JR*$_z$ where J is a group 15 or 16 element, preferably N, P, O or S (preferably N or O, preferably N), and R* is a C$_1$ to C$_{20}$ hydrocarbyl group. Typically, a linear branched or cyclic hydrocarbyl group having from one to twenty carbon atoms (such as methyl, ethyl, propyl, butyl, pentyl, hexyl, heptyl, octyl, nonyl, decyl, undecyl, dodecyl, or an isomer thereof, including t-butyl, cyclododecyl, cyclooctyl and the like) and z is 1 or 2.

In an embodiment, where m is 1, n is preferably 1 and G is a heteroatom group represented by the formula JR*$_z$ where J is a group 15 or 16 element, preferably N, P, O or S (preferably N or O, preferably N), and R* is a linear branched or cyclic hydrocarbyl group having from one to twenty carbon atoms (such as methyl, ethyl, propyl, butyl, pentyl, hexyl, heptyl, octyl, nonyl, decyl, undecyl, dodecyl or an isomer thereof, including t-butyl, cyclodecyl, cyclooctyl and the like) and z is 1 or 2, preferably JR*z is cyclododecyl amido, t-butyl amido, and or 1-adamantyl amido.

In an embodiment, when m is 2 or 3, n is 0.

In an embodiment each X$^5$ may be, independently, a halide, a hydride, an alkyl group, an alkenyl group or an arylalkyl group.

Alternately, each X$^5$ is, independently, selected from the group consisting of hydrocarbyl radicals having from 1 to 20 carbon atoms, aryls, hydrides, amides, alkoxides, sulfides, phosphides, halides, dienes, amines, phosphines, ethers, and a combination thereof, (two X$^5$'s may form a part of a fused ring or a ring system), preferably each X$^5$ is independently selected from halides, aryls and C$_1$ to C$_5$ alkyl groups, preferably each X$^5$ is a phenyl, methyl, ethyl, propyl, butyl, pentyl, or chloro group.

Typically, each Cp group is, independently, a substituted or unsubstituted cyclopentadiene, a substituted or unsubstituted indene, or a substituted or unsubstituted fluorene.

Independently, each Cp group may be substituted with a combination of substituent groups R$^{11}$. Non-limiting examples of substituent groups R$^{11}$ include one or more from the group selected from hydrogen, or linear, branched alkyl radicals, or alkenyl radicals, alkynyl radicals, cycloalkyl radicals or aryl radicals, acyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl- carbamoyl radicals, acyloxy radicals, acylamino radicals, aroylamino radicals, straight, branched or cyclic, alkylene radicals, or combination thereof. In a preferred embodiment, substituent groups $R^{11}$ have up to 50 non-hydrogen atoms, preferably from 1 to 30 carbons, which can also be substituted with halogens or heteroatoms or the like. Non-limiting examples of alkyl substituents $R^{11}$ include methyl, ethyl, propyl, butyl, pentyl, hexyl, cyclopentyl, cyclohexyl, benzyl or phenyl groups and the like, including all their isomers, for example, tertiary butyl, isopropyl and the like. Other hydrocarbyl radicals include fluoromethyl, fluoroethyl, difluoroethyl, iodopropyl, bromohexyl chlorobenzyl and hydrocarbyl substituted organometalloid radicals including trimethylsilyl, trimethylgermyl, methyldiethylsilyl and the like; and halocarbyl-substituted organometalloid radicals including tris (trifluoromethyl)-silyl, methylbis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R include the atoms carbon, silicon, boron, aluminum, nitrogen, phosphorus, oxygen, tin, sulfur, germanium and the like, including olefins such as, but not limited to, olefinically unsaturated substituents including vinyl-terminated ligands, for example but-3-enyl, prop-2-enyl, hex-5-enyl and the like. Also, at least two $R^{11}$ groups, preferably two adjacent $R^{11}$ groups, may be joined to form a ring structure having from 3 to 30 atoms selected from carbon, nitrogen, oxygen, phosphorus, silicon, germanium, aluminum, boron or a combination thereof.

In an embodiment of the Cp group, the substituent(s) $R^{11}$ are, independently, hydrocarbyl groups, heteroatoms, or heteroatom containing groups, such as methyl, ethyl, propyl, butyl, pentyl, hexyl, heptyl, octyl, nonyl, decyl, undecyl, dodecyl or an isomer thereof, N, O, S, P, or a $C_1$ to $C_{20}$ hydrocarbyl substituted with an N, O, S and or P heteroatom or heteroatom containing group (typically having up to 12 atoms, including the N, O, S and P heteroatoms).

Non-limiting examples of Cp groups include cyclopentadienyl ligands, cyclopentaphenanthreneyl ligands, indenyl ligands, benzindenyl ligands, fluorenyl ligands, octahydrofluorenyl ligands, cyclooctatetraenyl ligands, cyclopentacyclododecene ligands, azenyl ligands, azulene ligands, pentalene ligands, phosphoyl ligands, phosphinimine ligands (PCT International Publication WO 99/40125), pyrrolyl ligands, pyrazolyl ligands, carbazolyl ligands, borabenzene ligands and the like, including hydrogenated versions thereof, for example tetrahydroindenyl ligands. In another embodiment, each Cp may, independently comprise one or more heteroatoms, for example, nitrogen, silicon, boron, germanium, sulfur and phosphorus, in combination with carbon atoms to form an open, acyclic, or preferably a fused, ring or ring system, for example, a heterocyclopentadienyl ancillary ligand. Other Cp ligands include but are not limited to porphyrins, phthalocyanines, corrins and other polyazamacrocycles.

Preferably, T is present and is a bridging group containing at least one Group 13, 14, 15, or 16 elements, in particular boron or a Group 14, 15 or 16 element. Examples of suitable bridging groups include $P(=S)R^{12}$, $P(=Se) R^{12}$, $P(=O)$ $R^{12}$, $R^{12}_2C$, $R^{12}_2Si$, $R^{12}_2Ge$, $R^{12}_2CCR^{12}_2$, $R^{12}_2CCR^{12}_2CR^{12}_2$, $R^{12}_2CCR^{12}_2CR^{12}_2CR^{12}_2$, $R^{12}C=CR^{12}$, $R^{12}C=CR^{12}CR^{12}_2$, $R^{12}_2CCR^{12}=CR^{12}CR^{12}_2$, $R^{12}C=CR^{12}CR^{12}_2=CR^{12}$, $R^{12}C=CR^{12}CR^{12}_2CR^{12}_2$, $R^{12}_2CSiR^{12}_2$, $R^{12}_2SiSiR^{12}_2$, $R^{12}_2SiOSiR^{12}_2$, $R^{12}_2CSiR^{12}_2CR^{12}_2$, $R^{12}_2SiCR^{12}_2SiR^{12}_2$, $R^{12}C=CR^{12}SiR^{12}_2$, $R^{12}_2CGeR^{12}_2$, $R^{12}_2GeGeR^{12}_2$, $R^{12}_2CGeR^{12}_2CR^{12}_2$, $R^{12}_2GeCR^{12}_2GeR^{12}_2$, $R^{12}_2SiGeR^{12}_2$, $R^{12}C=CR^{12}GeR^{12}_2$, $R^{12}B$, $R^{12}_2C-BR^{12}$, $R^{12}_2C-BR^{12}-CR^{12}_2$, $R^{12}_2C-O-CR^{12}_2$, $R^{12}_2CR^{12}_2C-O-CR^{12}_2CR^{12}_2$, $R^{12}_2C-O-CR^{12}_2CR^{12}_2$, $R^{12}_2C-O-CR^{12}=CR^{12}$, $R^{12}_2C-S-CR^{12}_2$, $R^{12}_2CR^{12}_2C-S-CR^{12}_2CR^{12}_2$, $R^{12}_2C-S-CR^{12}_2CR^{12}_2$, $R^{12}_2C-S-CR^{12}=CR^{12}$, $R^{12}_2C-Se-CR^{12}_2$, $R^{12}_2CR^{12}_2C-Se-CR^{12}_2CR^{12}_2$, $R^{12}_2C-Se-CR^{12}_2CR^{12}_2$, $R^{12}_2C-Se-CR^{12}=CR^{12}$, $R^{12}_2C-N=CR^{12}$, $R^{12}_2C-NR^{12}-CR^{12}_2$, $R^{12}_2C-NR^{12}-CR^{12}_2CR^{12}_2$, $R^{12}_2C-NR^{12}-CR^{12}=CR^{12}$, $R^{12}_2CR^{12}_2C-NR^{12}-CR^{12}_2CR^{12}_2$, $R^{12}_2C-P=CR^{12}$, $R^{12}_2C-PR^{12}-CR^{12}_2$, O, S, Se, Te, $NR^{12}$, $PR^{12}$, $AsR^{12}$, $SbR^{12}$, O—O, S—S, $R^{12}N-NR^{12}$, $R^{12}P-PR^{12}$, O—S, O—$NR''$, O—$PR^{12}$, S—$NR^{12}$, S—$PR^{12}$, and $R^{12}N-PR^{12}$ where $R^{12}$ is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent $R^{12}$ may join to form a substituted or unsubstituted, saturated, partially unsaturated or aromatic, cyclic or polycyclic substituent. Preferred examples for the bridging group T include $CH_2$, $CH_2CH_2$, $SiMe_2$, $SiPh_2$, $SiMePh$, $Si(CH_2)_3$, $Si(CH_2)_4$, O, S, NPh, PPh, NMe, PMe, NEt, NPr, NBu, PEt, PPr, $Me_2SiOSiMe_2$, and PBu.

In a preferred embodiment of the invention in any embodiment of any formula described herein, T is represented by the formula $R^{14}_2J$ or $(R^{14}_2J)_2$, where J is C, Si, or Ge, and each $R^{14}$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two $R^{14}$ can form a cyclic structure including aromatic, partially saturated, or saturated cyclic or fused ring system. Preferably, T is a bridging group comprising carbon or silica, such as dialkylsilyl, preferably T is selected from $CH_2$, $CH_2CH_2$, $C(CH_3)_2$, $SiMe_2$, $SiPh_2$, $SiMePh$, silylcyclobutyl $(Si(CH_2)_3)$, $(Ph)_2C$, $(p-(Et)_3SiPh)_2C$, $Me_2SiOSiMe_2$, and cyclopentasilylene (Si $(CH_2)_4$).

Useful bridged metallocene compounds having one cyclopentadienyl ring include those represented by the formula:

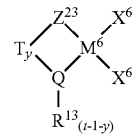

wherein $M^6$ is the same as $M^6$ described above. Preferably, $M^6$ is titanium, zirconium or hafnium, preferably titanium; $Z^{23}$ is a substituted or unsubstituted Cp group (useful $Z^{23}$ groups are represented by the formula: $(C_5H_{4-d}S^*_d)$, where d is 1, 2, 3 or 4, $S^*$ is hydrocarbyl groups, heteroatoms, or heteroatom containing groups, such as methyl, ethyl, propyl, butyl, pentyl, hexyl, heptyl, octyl, nonyl, decyl, undecyl, dodecyl or an isomer thereof, N, O, S, P, or a $C_1$ to $C_{20}$ hydrocarbyl substituted with an N, O, S and or P heteroatom or heteroatom containing group (typically having up to 12 atoms, including the N, O, S and P heteroatoms) and two S* may form a cyclic or multicyclic group, preferably $Z^{23}$ is tetramethylcyclopentadienyl;

T is a bridging group as described above that is bonded to $Z^{23}$ and Q, y is one;

Q is a heteroatom with a coordination number of three from Group 15 or with a coordination number of two from Group 16 of the Periodic Table of Elements, such as N, O, S or P and preferably Q is nitrogen;

$R^{13}$ is selected from a $C_3$-$C_{100}$ substituted or unsubstituted monocyclic or polycyclic ring structure substituent that is partially unsaturated, unsaturated or aromatic; or a $C_2$-$C_{100}$ substituted or unsubstituted, unsaturated or partially unsaturated, linear or branched alicyclic hydrocarbyl substituent; or a $C_1$-$C_{100}$ substituted or unsubstituted saturated hydrocarbyl radical (preferably $R^{13}$ is selected from methyl, ethyl, all propyl isomers, all butyl isomers, phenyl, benzyl, phenethyl, 1-adamantyl, cyclododecyl, cyclohexyl and norbornyl);

t is the coordination number of the heteroatom Q where "t-1-y" indicates the number of $R^{13}$ substituents bonded to Q; and each $X^6$ is, independently, a univalent anionic ligand, or two $X^6$ are joined and bound to the metal atom to form a metallocycle ring, or two $X^6$ are joined to form a chelating ligand, a diene ligand, or an alkylidene ligand.

Illustrative, but not limiting, examples of preferred monocyclopentadienyl metallocenes for use in this invention's catalyst system include:
dimethylsilyl (tetramethylcyclopentadienyl)(cyclododecylamido)titanium dimethyl, dimethylsilyl (tetramethylcyclopentadienyl)(cyclododecylamido)titanium dichloride, dimethylsilyl (tetramethylcyclopentadienyl)(t-butylamido) titanium dimethyl, dimethylsilyl (tetramethylcyclopentadienyl)(t-butylamido)titanium dichloride, $\mu$-$(CH_3)_2$Si(cyclopentadienyl)(1-adamantylamido)$M^7(R^{15})_2$; $\mu$-$(CH_3)_2$Si(3-tertbutylcyclopentadienyl)(1-adamantylamido)$M^7(R^{15})_2$; $\mu$-$(CH_3)_2$(tetramethylcyclopentadienyl)(1-adamantylamido)$M^7(R^{15})_2$; $\mu$-$(CH_3)_2$Si(tetramethylcyclopentadienyl)(1-adamantylamido)$M^7$ $(R^{15})_2$; $\mu$-$(CH_3)_2$C(tetramethylcyclopentadienyl)(1-adamantylamido)$M^7(R^{15})_2$; $\mu$-$(CH_3)_2$Si(tetramethylcyclopentadienyl)(1-tertbutylamido)$M^7(R^{15})_2$; $\mu$-$(CH_3)_2$Si(fluorenyl)(1-tertbutylamido)$M^7(R^{15})_2$; $\mu$-$(CH_3)_2$Si (tetramethylcyclopentadienyl)(1-cyclododecylamido)$M^7$ $(R^{15})_2$; and $\mu$-$(C_6H_5)_2$C(tetramethylcyclopentadienyl)(1-cyclododecylamido)$M^7(R^{15})_2$; where $M^7$ is selected from a group consisting of Ti, Zr, and Hf and $R^{15}$ is selected from halogen or $C_1$ to $C_5$ alkyl, preferably $R^{15}$ is a methyl group.

Useful metallocenes having two cyclopentadienyl rings are represented by the formula:

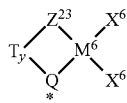

wherein $M^6$ is the same as $M^6$ described above, preferably $M^6$ is titanium, zirconium or hafnium, preferably Zr or Hf; $Z^{23}$ and Q* are, independently, a substituted or unsubstituted Cp group (useful $Z^{23}$ and Q* groups are represented by the formula: $(C_5H_{4-d}S^*_d)$, where d is 1, 2, 3 or 4, S* is hydrocarbyl groups, heteroatoms, or heteroatom containing groups, such as methyl, ethyl, propyl, butyl, pentyl, hexyl, heptyl, octyl, nonyl, decyl, undecyl, dodecyl or an isomer thereof, N, O, S, P, or a $C_1$ to $C_{20}$ hydrocarbyl substituted with an N, O, S and or P heteroatom or heteroatom containing group (typically having up to 12 atoms, including the N, O, S and P heteroatoms) and two S* may form a cyclic or multicyclic group;

T is a bridging group as described above that is bonded to $Z^{23}$ and Q*, y is zero or one; and each $X^6$ is, independently, a univalent anionic ligand, or two $X^6$ are joined and bound to the metal atom to form a metallocycle ring, or two $X^6$ are joined to form a chelating ligand, a diene ligand, or an alkylidene ligand provided that when y is one then at least one of $Z^{23}$ and Q* is preferably not an indene group, alternately both of $Z^{23}$ and Q* are not indene. In an alternate embodiment, when y is one, $Z^{23}$ and Q* are not 2, 4 substituted indene, preferably are not 2-methyl, 4-phenyl indene.

Particularly useful biscyclopentadienyl catalysts include: Bis(tetrahydroindene)Hf Me$_2$; B is (1-butyl,3-methylcyclopentadienyl)ZrCl$_2$; Bis-(n-butylcyclopentadienyl)ZrCl$_2$; (Dimethylsilyl)$_2$O bis(indenyl)ZrCl$_2$; Dimethylsilyl(3-(3-methylbutyl)cyclopentadienyl)(2,3,4,5-tetramethylcyclopentadienyl)ZrCl$_2$; Dimethylsilylbis(tetrahydroindenyl) ZrCl$_2$; Dimethylsilyl-(3-phenyl-indenyl) (tetramethylcyclopentadienyl)ZrCl$_2$; Dimethylsilyl(3-neopentylcyclopentadienyl)(tetramethylcyclopentadienyl) HfCl$_2$; Tetramethyldisilylene bis(4-(3,5-di-tert-butylphenyl)-indenyl)ZrCl$_2$; and Cyclopentadienyl(1,3-diphenylcyclopentadienyl)ZrCl$_2$.

Particularly useful metallocenes are those selected from the group consisting of: bis(cyclopentadienyl)zirconium dichloride, bis(pentamethylcyclopentadienyl)zirconium dichloride, bis(pentamethylcyclopentadienyl)zirconium dimethyl, bis(pentamethylcyclopentadienyl)hafnium dichloride, bis(pentamethylcyclopentadienyl)zirconium dimethyl, bis(1-methyl-3-n-butylcyclopentadienyl)zirconium dichloride, bis(1-methyl-3-n-butylcyclopentadienyl)zirconium dimethyl, bis(1-methyl-3-n-butylcyclopentadienyl)hafnium dichloride, bis(1-methyl-3-n-butylcyclopentadienyl)zirconium dimethyl, bis(indenyl)zirconium dichloride, bis(indenyl)zirconium dimethyl, bis(tetrahydro-1-indenyl)zirconium dichloride, bis(tetrahydro-1-indenyl)zirconium dimethyl, dimethylsilylbis(tetrahydroindenyl)zirconium dichloride, dimethylsilylbis(tetrahydroindenyl)zirconium dimethyl, dimethylsilylbis(indenyl)zirconium dichloride, dimethylsilyl(bisindenyl)zirconium dimethyl, dimethylsilyl-bis(cyclopentadienyl)zirconium dichloride, and dimethylsilylbis(cyclopentadienyl)zirconium dimethyl, and combinations thereof.

Particularly useful combinations of catalysts include: SiMe$_2$(Me$_4$Cp)(cC$_{12}$N)TiMe$_2$ and bis(1-Bu,3-Me-Cp) ZrCl$_2$; SiMe$_2$(Me$_4$Cp)(cC$_{12}$N)TiMe$_2$ and (SiMe$_2$) bis(indenyl)ZrCl$_2$; SiMe$_2$(Me$_4$Cp)(cC$_{12}$N)TiMe$_2$ and (SiMe$_2$)$_2$O bis (indenyl)ZrCl$_2$; SiMe$_2$(Me$_4$Cp)(cC$_{12}$N)TiMe$_2$ and (SiMe$_2$)$_2$O bis(indenyl)ZrMe$_2$; SiMe$_2$(Me$_4$Cp)(cC$_{12}$N) TiMe$_2$ and SiMe$_2$(3-neopentylCp)((Me$_4$Cp)HfCl$_2$; SiMe$_2$ (Me$_4$Cp)(cC$_{12}$N)TiMe$_2$ and SiMe$_2$(3-neopentylcyclopentadienyl)(Me$_4$Cp)HfMe$_2$; SiMe$_2$(Me$_4$Cp)(1-adamantylamido) TiMe$_2$ and bis(1-Bu,3-MeCp)ZrCl$_2$; and SiMe$_2$(Me$_4$Cp)(1-t-butylamido)TiMe$_2$ and bis(1-Bu,3-MeCp)ZrCl$_2$.

Synthesis of monocyclopentadienyl complexes is known in the art, and for example, has been disclosed in PCT International Publication No. WO 93/19103 and U.S. Pat. Nos. 5,096,867 and 5,264,405.

Synthesis of bis cyclopentadienyl complexes is known in the art, and for example, has been disclosed in and U.S. Pat. Nos. 4,530,914; 4,542,199; 4,769,910; 4,808,561; 4,871, 705; 4,933,403; 4,937,299; 5,017,714; 5,026,798; 5,057, 475; 5,120,867; 5,278,119; 5,304,614; 5,324,800; 5,350,723; 5,391,790; and 7,141,632, each fully incorporated herein by reference.

This invention can also be practiced with Ziegler Natta catalysts in combination with the supports described herein to produce olefin polymers.

Olefin polymers may generally be produced using Ziegler-Natta catalysts comprising 1) a solid titanium catalyst component comprising a titanium compound, a magnesium compound, and an internal electron donor; 2) a co-catalyst such as an organoaluminum compound, and 3) external electron donor(s). Ziegler-Natta catalysts, catalyst systems, and preparations thereof useful in the practice of the present invention include supported catalyst systems described in U.S. Pat. Nos. 4,990,479, 5,159,021 and WO 00/44795, preferably including solid titanium and or magnesium. For example, useful Ziegler-Natta catalysts are typically composed of a transition metal compound from groups 4, 5, 6 and/or 7 (preferably group 4) and an organometallic compound of a metal from groups 11, 12 and/or 13 (preferably group 13) of the periodic table. Well-known examples include $TiCl_3$-$Et_2AlCl$, $AlR_3$—$TiCl_4$ wherein Et is an ethyl group and R represents an alkyl group, typically a C1 to C20 alkyl group, such as methyl, ethyl, propyl, butyl, pentyl, hexyl, octyl and the like. These catalysts include mixtures of halides of transition metals, especially titanium, chromium, vanadium, and zirconium, with organic derivatives of nontransition metals, particularly alkyl aluminum compounds.

Briefly, the Ziegler-Natta catalysts can be obtained by: (1) suspending a dialkoxy magnesium compound in an aromatic hydrocarbon that is liquid at ambient temperatures; (2) contacting the dialkoxy magnesium-hydrocarbon composition with a titanium halide and with a diester of an aromatic dicarboxylic acid; and (3) contacting the resulting functionalized dialkoxy magnesiumhydrocarbon composition of step (2) with additional titanium halide.

The Ziegler-Natta catalyst is typically combined with a co-catalyst which is preferably an organoaluminum compound that is halogen free. Suitable halogen free organoaluminum compounds are, in particular, branched unsubstituted alkylaluminum compounds of the formula $AlR_3$, where R denotes an alkyl radical having 1 to 20 carbon atoms (preferably methyl, ethyl, propyl, butyl, pentyl, hexyl, octyl and the like), such as for example, trimethylaluminum, triethylaluminum, triisobutylaluminum and tridiisobutylaluminum. Additional compounds that are suitable for use as a cocatalyst are readily available and amply disclosed in the prior art including U.S. Pat. No. 4,990,477, which is incorporated herein by reference. The same or different Ziegler-Natta catalyst(s) can be used in both the initial and subsequent polymerization steps. In a preferred embodiment, the solid catalyst is a magnesium supported $TiCl_4$ catalyst and the organoaluminum co-catalyst is triethylaluminum.

Electron donors are also typically used in two ways in the formation of ZieglerNatta catalysts and catalyst systems. An internal electron donor may be used in the formation reaction of the catalyst as the transition metal halide is reacted with the metal hydride or metal alkyl. Examples of internal electron donors include amines, amides, ethers, esters, aromatic esters, ketones, nitriles, phosphines, stilbenes, arsines, phosphoramides, thioethers, thioesters, aldehydes, alcoholates, and salts of organic acids. In conjunction with an internal donor, an external electron donor may also used in combination with a catalyst. External electron donors often affect the level of stereoregularity in polymerization reactions.

The second use for an electron donor in a catalyst system is as an external electron donor and stereoregulator in the polymerization reaction. The same compound may be used in both instances, although typically they are different. Preferred External electron donor materials may include organic silicon compounds, e.g. tetraethoxysilane (TEOS) and dicyclopentydimethoxysilane (DCPMS). Internal and external-type electron donors are described, for example, in U.S. Pat. No. 4,535,068, which is incorporated herein by reference. The use of organic silicon compounds as external electron donors are described, for example, in U.S. Pat. Nos. 4,218,339, 4,395,360, 4,328,122, 4,473,660; 6,133,385; and 6,127,303, all of which are incorporated herein by reference. Particularly useful electron donors include external electron donors used as stereoregulators, in combination with ZieglerNatta catalysts.

A particularly useful Ziegler-Natta catalyst is a magnesium chloride supported titanium catalyst selected from the group of THC-C type catalyst solid systems available from Toho Titanium Corporation of Japan. Particularly preferred donor systems include those described in U.S. Pat. No. 6,087,459, such as for example, a blend of propyltriethoxysilane (PTES) and dicyclopentyldimethoxysilane (DCPMS), typically a 95/5 mole % blend. Another useful donor is methylcyclohexyl di-methoxysilane (MCMS).

A particular Ziegler-Natta catalyst may produce better results when paired with a particular group of electron donors. Examples of this paring of catalyst and electron donors are disclosed in U.S. Pat. Nos. 4,562,173 and 4,547,552, which are incorporated by reference herein.

In certain preferred embodiments described herein one catalyst compound is used, e.g., the catalyst compounds are not different. For purposes of this invention one catalyst compound is considered different from another if they differ by at least one atom. For example "bisindenyl zirconium dichloride" is different from "(indenyl)(2-methylindenyl) zirconium dichloride" which is different from "(indenyl)(2-methylindenyl) hafnium dichloride." Catalyst compounds that differ only by isomer are considered the same for purposes if this invention, e.g., rac-dimethylsilylbis(2-methyl 4-phenyl)hafnium dimethyl is considered to be the same as meso-dimethylsilylbis(2-methyl 4-phenyl)hafnium dimethyl.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds are preferably chosen such that the two are compatible. A simple screening method such as by $^1H$ or $^{13}C$ NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination, as described further below. If one or more transition metal compounds contain an $X^6$ ligand which is not a hydride, hydrocarbyl, or substituted hydrocarbyl, then the alumoxane should be contacted with the transition metal compounds prior to addition of the non-coordinating anion activator.

Where two catalyst compounds are used, the two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percentages, based upon the molecular weight of the pre-catalysts, are about 10 to about 99.9% A to about 0.1 to about 90% B, alternatively about 25 to about 99% A to about 0.5 to about 50% B, alternatively about 50 to about 99% A to about 1 to about 25% B, and alternatively about 75 to about 99% A to about 1 to about 10% B.

Typically, the catalyst compound is present on the support at from 0.01 micromols of catalyst per gram of support to 100 micromols of catalyst per gram of support (preferably from 0.1 micromols of catalyst per gram of support to 10 micromols of catalyst per gram of support, preferably from 1 micromols of catalyst per gram of support to 5 micromols of catalyst per grain of support, preferably from 3 micromols of catalyst per grain of support to 5 micromols of catalyst per gram of support.

Binder

The catalyst and orMOS material may optionally comprise a binder. Suitable binders, include but are not limited to silica, alumina, zirconia, titania, silica-alumina, cerium oxide, magnesium oxide, or combinations thereof. Thus, in another embodiment, an organosilica material comprising a catalyst material described herein is provided. The catalyst material may optionally comprise a binder or be self-bound. Suitable binders, include but are not limited to, active and inactive materials, synthetic or naturally occurring zeolites, as well as inorganic materials such as clays and/or oxides such as silica, alumina, zirconia, titania, silica-alumina, cerium oxide, magnesium oxide, or combinations thereof. In particular, the binder may be silica-alumina, alumina and/or a zeolite, particularly alumina. Silica-alumina may be either naturally occurring or in the form of gelatinous precipitates or gels including mixtures of silica and metal oxides. It should be noted it is recognized herein that the use of a material in conjunction with a zeolite binder material, i.e., combined therewith or present during its synthesis, which itself is catalytically active may change the conversion and/or selectivity of the finished catalyst. It is also recognized herein that inactive materials can suitably serve as diluents to control the amount of conversion if the present invention is employed in alkylation processes so that alkylation products can be obtained economically and orderly without employing other means for controlling the rate of reaction. These inactive materials may be incorporated into naturally occurring clays, e.g., bentonite and kaolin, to improve the crush strength of the catalyst under commercial operating conditions and function as binders or matrices for the catalyst. The catalysts described herein typically can comprise, in a composited form, a ratio of support material to binder material ranging from about 80 parts support material to 20 parts binder material to 20 parts support material to 80 parts binder material, all ratios being by weight, typically from 80:20 to 50:50 support material:binder material, prefer ably from 65:35 to 35:65. Compositing may be done by conventional means including mulling the materials together followed by extrusion of pelletizing into the desired finished catalyst particles.

Activators

In addition to the organosilica support and catalyst(s) described above, the catalyst system according to the present disclosure includes one or more activator compounds.

After the catalyst complexes described above are synthesized, catalyst compounds may be activated by combining them with activators in any manner known in the art and supported for use in slurry or gas phase polymerization. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

Alumoxane Activators

In one embodiment, alumoxane activators are utilized as an activator in the catalyst system. Alumoxanes are generally oligomeric compounds containing —Al($R^1$)—O— subunits, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A and described in U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

Non-Coordinating Anion Activators

A non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

In certain aspects, an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (PCT International Publication No. WO 98/43983), boric acid (U.S. Pat. No. 5,942,459), or combination thereof can be used. Neutral or ionic activators alone or in combination with alumoxane or modified alumoxane activators can also be used.

The catalyst systems of this invention can include at least one non-coordinating anion (NCA) activator.

In a preferred embodiment, boron containing NCA activators represented by the formula:

$$Z^{24}{}_{d^+}(A^{d-})$$

where: $Z^{24}$ is (L-H) or a reducible Lewis acid; L is a neutral Lewis base; H is hydrogen; (L-H) is a Bronsted acid; $A^{d-}$ is a boron containing non-coordinating anion having the charge d−; d is 1, 2, or 3.

The cation component, $Z^{24}{}_{d^+}$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z^{24}{}_{d^+}$ may also be a moiety such as silver, tropylium, carboniums, ferroceniums and mixtures, preferably carboniums and ferroceniums. Most preferably $Z^{24}{}_{d^+}$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl), preferably the reducible Lewis acids in formula above as "$Z^{24}$" include those represented by the formula: $(Ph_3C)$, where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably V is a triphenylcarbonium.

When $Z^{24}{}_{d^+}$ is the activating cation $(L-H)_d{}^+$, it is preferably a Bronsted acid, capable of donating a proton to the transition metal catalytic precursor resulting in a transition metal cation, including ammoniums, oxoniums, and/or phosphoniums.

The anion component $A^{d-}$ includes those having the formula $[M^{8k+}Q_n]^{d-}$ wherein k is 1, 2, or 3; n is 1, 2, 3, 4, 5, or 6 (preferably 1, 2, 3, or 4); n−k=d; $M^8$ is an element selected from Group 13 elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z^{24}{}_{d^+}$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3, 5-bis(trifluoromethyl)phenyl)borate, or triphenylcarbenium tetra(perfluorophenyl)borate.

A list of particularly useful Bulky Activators is described in U.S. Pat. No. 8,658,556, which is incorporated by reference herein.

In another embodiment, one or more of the NCA activators is chosen from the activators described in U.S. Pat. No. 6,211,105.

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. Nos. 5,153,157 and 5,453,410, European Patent Publication No. 0573120 B1, and International PCT Publications WO 94/07928, and WO 95/14044 which discuss the use of an alumoxane in combination with an ionizing activator).

Optional Scavengers, Chain Transfer Agents and/or Co-Activators

In addition to the activator compounds, scavengers, chain transfer agents or co-activators may be used. Aluminum alkyl compounds which may be utilized as scavengers or co-activators include, for example, one or more of those represented by the formula $AlR^{19}{}_3$, where each $R^{19}$ is, independently, a $C_1$-$C_8$ aliphatic radical, preferably methyl, ethyl, propyl, butyl, pentyl, hexyl octyl or an isomer thereof), especially trimethylaluminum, triethylaluminum, triisobutylaluminum, tri-n-hexylaluminum, tri-n-octylaluminum or mixtures thereof.

Useful chain transfer agents that may also be used herein are typically a compound represented by the formula $AlR^{20}{}_3$, $ZnR^{20}{}_2$ (where each $R^{20}$ is, independently, a $C_1$-$C_8$ aliphatic radical, preferably methyl, ethyl, propyl, butyl, pentyl, hexyl octyl or an isomer thereof) or a combination thereof, such as diethyl zinc, trimethylaluminum, triisobutylaluminum, trioctylaluminum, or a combination thereof.

Polymerization Processes

In certain embodiments, the catalytic systems of the present disclosure include organosilica materials as described herein as support matrices for separation and/or catalysis processes. For example, the organosilica materials may be supports in used for a polymerization process.

In embodiments herein, the invention relates to polymerization processes where monomer (such as propylene and or ethylene), and optionally comonomer, are contacted with a catalyst system comprising an activator, an organosilica material support and at least one catalyst, such as a metallocene compound, as described above. The support, catalyst compound, and activator may be combined in any order, and are combined typically prior to contacting with the monomers.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene and isomers thereof.

In an embodiment of the invention, the monomer comprises propylene and an optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups.

In another embodiment of the invention, the monomer comprises ethylene and optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes ($M_w$ less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes according to the present disclosure can be carried out in any manner known in the art. Any suspension, slurry, or gas phase polymerization process known in the art can be used. Such processes can be run in a batch, semi-batch, or continuous mode. Heterogeneous polymerization processes (such as gas phase and slurry phase processes) are preferred. A heterogeneous process is defined to be a process where the catalyst system is not soluble in the reaction media. Alternately the polymerization process is not homogeneous. A homogeneous polymerization process is defined to be a process where at least 90 wt % of the product is soluble in the reaction media. Alternately the polymerization process is not a bulk process is particularly preferred. A bulk process is defined to be a process where monomer concentration in all feeds to the reactor is 70 volume % or more). Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In some embodiments, hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In one embodiment of the invention, the polymerization is performed in the gas phase, preferably in a fluidized gas bed process. Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference.

In another embodiment of the invention, the polymerization is performed in the slurry phase. A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers, along with catalysts, are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used, the process is typically operated above the reaction diluent critical temperature and pressure. Often, a hexane or an isobutane medium is employed.

In an embodiment, a preferred polymerization technique useful in the invention is referred to as a particle form polymerization, or a slurry process where the temperature is kept below the temperature at which the polymer goes into solution. Such technique is known in the art, and described in for instance U.S. Pat. No. 3,248,179, which is fully incorporated herein by reference. A preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. In one embodiment 500 ppm or less of hydrogen is added, or 400 ppm or less or 300 ppm or less. In other embodiments at least 50 ppm of hydrogen is added, or 100 ppm or more, or 150 ppm or more.

The slurry reactor may be maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In certain embodiments, little or no alumoxane is used in the process to produce the polymers. Alumoxane is optionally present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the polymer, such as ethylene polymer. Preferably, scavenger (such as trialkyl aluminum, $Al^1R^{19}{}_3$ as defined above) is present at zero mol %, alternately the scavenger is present at a molar ratio of scavenger metal to transition metal of less than 100:1, preferably less than 50:1, preferably less than 15:1, preferably less than 10:1.

In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

In a preferred embodiment of the invention, the polymerization occurs within the mesopores of the organosilica material support and preferably the mesopores have an average diameter as discussed above, for example, from about 2 nm to about 50 nm, alternately about 3 nm to about 20 nm.

Polyolefin Products

This invention also relates to polymer compositions of matter produced by the methods described herein.

In a preferred embodiment of the invention, the process described herein produces homopolymers copolymers of one, two, three, four or more $C_2$ to $C_{40}$ olefin monomers, preferably $C_2$ to $C_{20}$ alpha olefin monomers. Particularly useful monomers include ethylene, propylene, butene, pentene, hexene, heptene, octene, nonene, decene, undecene, dodecene, isomers thereof and mixtures thereof.

Likewise, the process of this invention produces olefin polymers, preferably polyethylene and polypropylene homopolymers and copolymers. In a preferred embodiment, the polymers produced herein are homopolymers of ethylene or homopolymers of propylene.

Alternately, the polymers produced herein are copolymers of a $C_2$ to $C_{40}$ olefin and one, two or three or more different $C_2$ to $C_{40}$ olefins, (where the $C_2$ to $C_{40}$ olefins are preferably $C_3$ to $C_{20}$ olefins, preferably are $C_3$ to $C_{12}$ alpha-olefin, preferably are propylene, butene, hexene, octene, decene, dodecene, preferably propylene, butene, hexene, octene or a mixture thereof).

Alternately, the polymers produced herein are copolymers of ethylene preferably having from 0 to 25 mole % (alternately from 0.5 to 20 mole %, alternately from 1 to 15 mole %, preferably from 3 to 10 mole %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene).

Alternately, the polymers produced herein are copolymers of are copolymers of propylene preferably having from 0 to 25 mole % (alternately from 0.5 to 20 mole %, alternately from 1 to 15 mole %, preferably from 3 to 10 mole %) of one or more of $C_2$ or $C_4$ to $C_{20}$ olefin comonomers (preferably ethylene or $C_4$ to $C_{12}$ alpha-olefin, preferably ethylene, butene, hexene, octene, decene, dodecene, preferably ethylene, butene, hexene, octene).

Typically, the polymers produced herein have an $M_w$ of 5,000 to 1,000,000 g/mol (preferably 25,000 to 750,000 g/mol, preferably 50,000 to 500,000 g/mol), and/or an $M_w/M_n$ of greater than 1 to 40 (alternately 1.2 to 20, alternately 1.3 to 10, alternately 1.4 to 5, 1.5 to 4, alternately 1.5 to 3).

In a preferred embodiment the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

Unless otherwise indicated $M_w$, $M_n$, MWD are determined by GPC as described in U.S. Publication No. 2006/0173123, at pages 24-25, paragraphs [0334] to [0341].

In a preferred embodiment the polymer produced herein has a composition distribution breadth index (CDBI) of 50% or more, preferably 60% or more, preferably 70% or more. CDBI is a measure of the composition distribution of monomer within the polymer chains and is measured by the procedure described in PCT International Publication No. WO 93/03093, specifically at columns 7 and 8 as well as in Wild et al, J. Poly. Sci., Poly. Phys. Ed., Vol. 20, p. 441 (1982) and U.S. Pat. No. 5,008,204, including fractions having a weight average molecular weight ($M_w$) below 15,000 are ignored when determining CDBI.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

Films

Specifically, any of the foregoing polymers, such as the foregoing polypropylenes or blends thereof, may be used in a variety of end-use applications. Such applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents.

VI. EXPERIMENTAL

Examples

The following examples are merely illustrative, and do not limit this disclosure in any way.

General Methods

Small Angle X-ray Diffraction Analysis

X-ray powder diffraction (XRD) patterns were collected on a PANalytical X'pert diffractometer equipped with an accessory for low angle measurements. XRD analyses were recorded using the Cu Ka (=1.5405980 Å) line in the 2θ range from 0.5 to 10° with a step size of 0.0167° and a counting time of 1.2 s.

$^{29}$Si MAS NMR, $^{13}$C CPMAS NMR and $^{27}$Al MAS NMR Spectra

The $^{29}$Si MAS NMR spectra were recorded on a Varian InfinityPlus-400 spectrometer (operating at 9.4T) and Varian InfinityPlus-500 (operating at 11.74T), corresponding to $^{29}$Si Larmor frequencies of 79.4 MHz and 99.2 MHz, respectively, with a 7.5 mm MAS probe heads using 5 kHz spinning, 4.0 μs 90° pulses, and at least 60 s recycle delay, with proton decoupling during data acquisition. The $^{29}$Si chemical shifts are referenced with respect to an external tetramethyl silane ($\delta_{si}$=0.0 ppm). The $^{13}$C CPMAS NMR spectra were recorded on a Varian InfinityPlus-500 spectrometer corresponding to $^{13}$C Larmor frequency of 125 MHz, with 1.6 mm MAS probe head using 40 kHz spinning, $^1$H-$^{13}$C cross-polarization (CP) contact time of 1 ms, a recycle delay of 1 s, with proton decoupling during data acquisition. The $^{13}$C chemical shifts are referenced with respect to an external tetramethyl silane ($\delta_C$=0.0 ppm). The $^{27}$Al MAS NMR spectra were recorded on a Varian InfinityPlus-500 corresponding to $^{27}$Al Larmor frequency of 130.1 MHz using a 4 mm MAS probe head using 12 kHz spinning, with a $\pi/12$ radian pulse length, with proton decoupling during data acquisition, and a recycle delay of 0.3 s. The chemical shifts are referenced with respect to an external solution of Al(H$_2$O)$_6^{3+}$ ($\delta_{Al}$=0.0 ppm). All NMR spectra were recorded at room temperature using air for spinning.

$^1$H NMR

Products were characterized by $^1$H NMR as follows: A Bruker 400 MHz Advance III Spectrometer was used. In certain experiments, $^1$H NMR data are collected at 22° C. in a 5 mm probe using the 400 MHz Bruker spectrometer with deuterated solvent in which the sample is completely soluble. Data is recorded using a maximum pulse width of 45°, 8 seconds between pulses and signal averaging 16 transients.

Thermal Gravimetric Analysis (TGA)

Thermal stability results were recorded on Q5000 TGA. Ramp rate was 5° C./min, temperature range was from 25° C. to 800° C. All the samples were tested in both air and nitrogen.

Example 1—Organosilica Material Syntheses Using Formula [R$^3$R$^4$SiCH$_2$]$_3$ (IA) in Basic or Acidic Media 1A. Synthesis Using [(EtO)$_2$SiCH$_2$]$_3$ in Basic Aqueous Medium—without Surfactant A solution with 18.6 g of 30% NH$_4$OH and 23.76 g deionized water (DI) water was made. The pH of the solution was 12.55. To the solution, 3.0 g of 1,1,3,3,5,5-hexaethoxy-1,3,5-trisilacyclohexane ([(EtO)$_2$SiCH$_2$]$_3$) was added, producing a mixture having the molar composition:

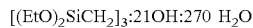
[(EtO)$_2$SiCH$_2$]$_3$:21OH:270 H$_2$O and stirred for 1 day at room temperature (20-25° C.). The solution was transferred to an autoclave and aged at 80° C.-90° C. for 1 day to produce a gel. The gel was dried at 80° C. in a vacuum to remove most of the water and then fully dried at 110° C. for three hours. This produced Sample 1A as a clear solid, which was converted to white powder after grinding. No surface directing agent or porogen were used in this preparation.

The procedure was repeated with the following molar composition:

4.0[(EtO)$_2$SiCH$_2$]$_3$:21 OH:270 H$_2$O to produce Sample 1B. XRD, TGA weight loss studies, Nitrogen adsorption/desorption analysis and $^{29}$Si MAS NMR were performed on Sample 1A. Those data are reported in U.S. Ser. No. 14/965,992; filed Dec. 11, 2015.

1B. Comparative—Synthesis Using [(EtO)$_2$SiCH$_2$]$_3$ in Basic Aqueous Medium with Surfactant In this example, an organosilica material was prepared according to Landskron, K., et al., Science 302:266-269 (2003). Cetyltrimethylammonium bromide (CTMABr, 0.9 mmol, 0.32 g, Aldrich) was dissolved in a mixture of 2.16 g NH$_4$OH (35 wt %) and 3.96 g de-ionized water at 20° C. to form a solution. [(EtO)$_2$SiCH$_2$]$_3$ (1.26 mmol, 0.5 g) was added to the solution, producing a solution having the molar composition:

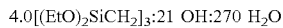
[(EtO)$_2$SiCH$_2$]$_3$:17OH:236 H$_2$O:0.7 CTMABr which was stirred for 1 day at 20° C. and a white precipitate formed. Afterwards, the solution was aged for 1 day at 80° C. Then the precipitate was filtered off and washed with water. The sample was then stirred for 48 hours in a solution of 12 g HCl (36 wt %) and 80 g of methanol. The sample was then filtered off again and washed with MeOH, resulting in Comparative Sample 2. XRD, TGA weight loss studies, and Nitrogen adsorption/desorption analysis were performed Comparative Sample 2. Those data are reported in U.S. Ser. No. 14/965,992; filed Dec. 11, 2015. Compared to the XRD pattern of Sample 1A, the XRD pattern of Comparative Sample 2 exhibits a shoulder at about 3 degrees 2θ. The surface area, average pore diameter, and pore volume obtained by the nitrogen adsorption/desorption analysis for Sample 1A and Comparative Sample 2 are shown below in Table 1.

TABLE 1

| Material | BET (m$^2$/g) | Pore Diameter (nm) | Pore Volume (cc/g) |
|---|---|---|---|
| Comparative Sample 2 | 1520 | 3.02 | 1.07 |
| Sample 1A | 1410 | 3.18 | 0.92 |

Comparative Sample 2 was characterized with $^{29}$Si MAS NMR as shown and those data are reported in Those data are reported in U.S. Ser. No. 14/965,992; filed Dec. 11, 2015. As shown below in Table 2, Sample 1A had a higher silanol content (i.e., 47%) compared to Comparative Sample 2 (i.e., 41%).

TABLE 2

| | D$_1$ | D$_2$ | T sites | Si(OH)/Si |
|---|---|---|---|---|
| Sample 1A (%) | 45.6 | 96 50.4 | 4 | 47 |
| Comparative Sample 2(%) | 34.7 | 89 54.3 | 11 | 41 |

1C. Synthesis Using [(EtO)$_2$SiCH$_2$]$_3$ in Acidic Aqueous Medium—without Surfactant A 14 g HCl solution with a pH of 2 was made by adding 0.778 mol water and 0.14 mmol HCl. To the solution, 1.0 g (2.52 mmol) of [(EtO)$_2$SiCH$_2$]$_3$ was added producing a solution having the molar composition:

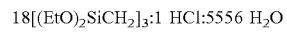
18[(EtO)$_2$SiCH$_2$]$_3$:1 HCl:5556 H$_2$O which was stirred for 1 day at room temperature (20-25° C.). The solution was transferred to an autoclave and aged at 94° C. for 1 day to produce a gel. The gel was dried in a vacuum at 120° C. overnight (16-24 hours) to produce Sample 3. No surface directing agent or porogen were used. XRD, Nitrogen adsorption/desorption were performed on Sample 3. Those data are reported in U.S. Ser. No. 14/965,992; filed Dec. 11, 2015.

1D. Synthesis Using [(EtO)$_2$SiCH$_2$]$_3$ and [CH$_3$EtOSiCH$_2$]$_3$

A solution with 6.21 g of 30% NH$_4$OH and 7.92 g DI water was made. To the solution, 0.6 g of [(EtO)$_2$SiCH$_2$]$_3$ 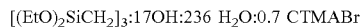 and 0.306 g of 1,3,5-trimethyl-1,3,5-triethoxy-1,3,5-trisilacyclohexane ([CH₃EtO₂SiCH₂]₃) was added producing a solution having the molar composition:

which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 4A was obtained. No structure directing agent or porogen were used.

Nitrogen Adsorption/Desorption Analysis

This above preparation method was repeated, except the relative ratio of [(EtO)₂SiCH₂]₃ (Reagent 1) to [CH₃EtO₂SiCH₂]₃ (Reagent 2) was varied. Nitrogen adsorption/desorption analysis was performed on each material and the results for each material is given below in Table 3.

TABLE 3

| Material | Reagent 1:Reagent 2 | BET (m²/g) | V (cc/g) | Pore Diameter (nm) |
|---|---|---|---|---|
| Sample 1A | 5:0 | 1410 | 0.915 | 3.18 |
| Sample 4A | 3:2 | 819 | 1.52 | 7.39 |
| Sample 4B | 4:1 | 1100 | 1.14 | 4.17 |
| Sample 4C | 2:3 | 460 | 1.09 | 13.9 |
| Sample 4D | 0:5 | 1.81 | 7.73E−03 | 68.8 |

As Reagent 2 increased, the average pore diameter was observed to increase, which without being bound by theory may be due to Reagent 2 containing less reactive —OR groups compared to Reagent 1. The porosity of the material decreased as Reagent 2 was greater than 60% (mol ratio). The materials in Table 3 were characterized with ²⁹Si MAS NMR, and those data are reported in U.S. Ser. No. 14/965,992; filed Dec. 11, 2015.

Example 2—Calcining Study

Sample 1A was calcined at temperatures of 300° C., 400° C., 500° C., and 600° C. in air to obtain Samples 1A(i), 1A(ii), 1A(iii) and 1A(iv), respectively. After calcining at 500° C. Sample 1A(iii) still exhibited good mesoporosity (e.g., 3 nm pore diameter and over 600 m²/g surface area).

Example 3: Synthesis of Catalyst System Including Organosilica Support Reacted with Alumoxane Activator and Catalyst Three mesoporous organosilica materials, Samples 1A, 3, and 4A are formed as described in Example 1. All materials to be tested as catalyst supports (Samples 1A, 3, and 4A) were dried at 250° C. overnight in a muffle furnace equipped with nitrogen purge. The dried organosilica supports were removed from the furnace while hot and allowed to cool under vacuum and then stored inside a nitrogen filled box.

In an initial experiment, Sample 1A was reacted with methyl alumoxane (MAO) to obtain an initial understanding of MAO reactivity with the organosilica support material and the level of reactivity —OH groups. MAO is methyl alumoxane (30 wt % in toluene) obtained from Albemarle. A first portion of the Sample 1A was used as received and reacted with MAO. High levels of MAO were found to react with Sample 1A organosilica support material. A second portion of the Sample 1A material was calcined at 200° C. prior to reaction with the MAO. These activated supports were then reacted with Catalyst 1 (1,3-Me,BuCp)₂ZrCl₂ and tested in slurry and phase reactors.

3A. Organosilica Material Reacted with Alumoxane Activator (Support 4)

0.5992 g Sample 1A was calcined at 200° C. overnight under vacuum was slurried in 17 mL of toluene. 1.36 g of MAO (30% wt solution in toluene) was added to the slurry. The slurry was heated to 70° C. for 1 hr. ¹H NMR analysis showed no MAO in solution. A second batch of MAO (1.0135 g) was added. The slurry was stirred for another 30 minutes. A second ¹H NMR revealed excess MAO. The slurry was filtered, washed three times with 15 mL of toluene each, washed twice with pentane, and dried under vacuum to give 1.0694 g of white solid.

3B. Organosilica Material Reacted with Alumoxane Activator (Support 5)

1.0250 g of Sample 1A was slurried in 20 mL of toluene. 4.680 g of MAO (30% wt solution in toluene) was added to the slurry. The slurry was heated to 70° C. for 1 hr. ¹H NMR analysis did not show any excess MAO. An additional batch of MAO (2.4965 g, 30 wt % solution in toluene) was then added to the slurry. The slurry was stirred for another 20 minutes. A second ¹H NMR showed a slight excess of MAO. The slurry was filtered, washed three times with 15 mL of toluene each, washed twice with pentane, and dried under vacuum to give 2.87 g of white solid. The resultant Support 5 is an organosilica support material reacted with MAO activator.

3D. Reaction with Metallocene Catalyst 0.5141 g of Support 5 produced in Example 3B was slurried in 15 mL of toluene. Catalyst 1 (1,3-Me,BuCp)₂ZrCl₂ (8.8 mg, 0.0203 mmol) was dissolved in 5 mL of toluene and added to the slurry. The slurry was stirred for 45 min. The slurry was filtered, washed three times with 15 mL of toluene each, washed twice with pentane, and dried under vacuum to give 0.4018 g of white solid (Sample 6).

3F. Reaction of Calcined Organosilica-Alumoxane with Metallocene Catalyst 0.4309 g of Support 4 produced in Example 3A was slurried in 15 mL of toluene. 7.4 mg, 0.0174 mmol of Catalyst 1 (1,3-Me,BuCp)₂ZrCl₂ was dissolved in 5 mL of toluene and added to the slurry. The slurry was stirred for 1 hr. The slurry was filtered, washed three times with 15 mL of toluene each, washed twice with pentane, and dried under vacuum to give 0.4011 g of white solid (Sample 8).

Example 4: Synthesis of Comparative Example of Methyl Alumoxane Supported Activator (SMAO) Catalyst System Ineos ES757 silica (741 g), dehydrated at 610° C., was added to a stirred (overhead mechanical conical stirrer) mixture of toluene (2 L) and methylaluminoxane solution (874 g; Albemarle, 30 wt % in toluene). The silica was chased with toluene (200 mL) then the mixture was heated to 90° C. for 3 hours. Afterwards, volatiles were removed by application of vacuum and mild heat (40° C.) overnight then the solid was allowed to cool to room temperature.

The catalyst support is then reacted with Catalyst 1 (1,3-Me,BuCp)₂ZrCl₂ in an amount that yield a supported catalyst containing approximately 0.35 wt % Zr. The resultant Comparative Sample 9 is a SMAO catalyst system.

Example 5: Synthesis of Catalyst System Including Organosilica Support Reacted with Alumoxane Activator and Catalyst Example 5A. Organosilica Material Reacted with Alumoxane Activator 0 g of Sample 3 was slurried in 20 mL of toluene in a 50 mL Celstir™ flask. 2.5 g of a 30 wt MAO solution in toluene was slowly added to the slurry. The slurry was stirred for 1 hr at 70° C. The slurry was filtered, rinsed with toluene, 10 mL, and dried under vacuum to give 1.15 g of white solid (Sample 10).

Example 5B. Reaction with Metallocene Catalyst

A 247 mg amount of Sample 10 was slurried in approximately 10 mL of toluene using a Celstir™ flask. Next, 4.3 mg (10 μmol) of Catalyst A (bis(1-me,3-n-propyl cyclopentadienyl)ZrCl$_2$) was added to the Celestir™ vessel from a stock solution (1 mg/g toluene). This mixture was stirred for three hours, after which the mixture was filtered using a glass frit. It was washed with two 10 mL portions of hexane and then dried under vacuum for two hours. The yield was 160 mg of off-white powder (Sample 11).

Example 6: Organosilica Support Material Reacted with Alumoxane Activator

Example 6A. Activation with Alumoxane 2.55 g of Sample 4A was slurried in about 20 mL of toluene in a 50 mL round bottom flask with a stir bar. While stirring, 9.9 mls of a 30 wt % MAO solution in toluene was added in four portions over several minutes. The slurry was heated to 70° C. for 1.5 hours. The solid was isolated by filtration, washed 2×20 mL with toluene and 2×20 mL pentane, then dried under vacuum at room temperature. The yield was 3.51 grams. The resultant Sample 12 is an organosilica support material reacted with MAO activator.

Example 6B. Activation with Alumoxane g of Sample 4A was slurried in about 20 mL of toluene in a 50 mL Celstir™ flask. While stirring, 9.9 mls of a 30 wt % MAO solution in toluene was added in four portions over several minutes. The slurry was heated to 70° C. for 1 hour. The solid was isolated by filtration, washed 2×20 mL with toluene and 2×20 mL pentane, then dried under vacuum at room temperature. The yield was 1.86 grams. The resultant Sample 13 is an organosilica support material reacted with MAO activator.

Example 6C. Reaction with Metallocene Catalyst

A 245 mg amount of Sample 13 was slurried in approximately 10 mL of toluene using a Celstir™ flask. Next, 4.3 mg (10 μmol) of Catalyst A (bis(1-methyl, 3-n-propyl cyclopentadienyl)ZrCl$_2$) was added to the Celestir™ vessel from a stock solution (1 mg/g toluene). This mixture was stirred for three hours, after which the mixture was filtered using a glass frit. It was washed with two 10 mL portions of hexane and then dried under vacuum for two hours. The yield was 240 mg of off-white powder (Sample 14).

Example 7: Synthesis of Catalyst System Including Organosilica Material Reacted with Alumoxane Activator (Example 11—Cat Prep—Bridged MCN)

490 mg of Sample 13 was slurried in approximately 5 mL of toluene using a Celstir™ vessel. Next, 8.5 mg (20 μmol) of Catalyst J (cyclobutylsilyl(cyclopentadienyl) (tetramethylcyclopentadienyl)ZrCl$_2$) was added to the Celestir™ vessel. This mixture was stirred for about 3 hours, after which the mixture was filtered using a glass frit. It was washed with two 10 mL portions of hexane and then dried under vacuum overnight. (Sample 23).

Example 8: Synthesis of Catalyst System Including Organosilica Material Reacted with Alumoxane Activator 0.5992 g of Sample 1A was calcined at 200° C. overnight under vacuum was slurried in 17 mL of toluene in a 50 ml Celstir™ flask. MAO (1.36 g of a 30% wt solution in toluene) was added to the slurry. The slurry was heated to 70° C. for 1 hr. $^1$H NMR analysis showed no MAO in solution. A second batch of MAO (1.01 g) was added. The slurry was stirred for another 30 minutes. A second $^1$H NMR revealed excess MAO. The slurry was filtered, washed three times with 15 mL of toluene each, washed twice with pentane, and dried under vacuum to give 1.07 g of white solid.

Example 9: Catalyst Activity During Polymerization with Organosilica Support Catalyst Systems Polymerization was performed in a 2 liter autoclave salt bed reactor. Reactor temperature was maintained at 85° C. throughout the run by a heating jacket. One hundred grams of agitated sodium chloride was used as the seed bed for the reaction. Hydrogen, ethylene, and hexene were added to the reactor, and catalyst was introduced using nitrogen. 2 ml of triisobutylaluminum was also added as a scavenger. Ethylene was added to the reactor to maintain 300 psi during the runs. Gas phase compositions were monitored by GC, and hexene and hydrogen were added as necessary to obtain the average compositions reported in Table 5. After 1 hour, the reaction was stopped and the salt bed was washed from the polymer using water. The resulting polymer was dried and weighed to obtain the final product.

Salt-bed reactor conditions for Catalyst-1 supported on MOS and on SMAO, as shown in Table 5 below.

TABLE 5

| | Sample 6 (MOS) | Comparative Sample 9 (SMAO) |
|---|---|---|
| Avg. Rx. N$_2$ Composition (mol %) | 28 | 27 |
| Avg. Rx. H$_2$ Composition (ppm) | 192 | 181 |
| Avg. Rx. C$_2$ Composition (mol %) | 66 | 67 |
| Avg. Rx. C$_6$ Composition (mol %) | 1.5 | 1.5 |
| Temperature (°85 C.) | 85 | 85 |
| Pressure (psi) | 300 | 300 |
| Catalyst Loading (mg) | 6 | 21 |
| Production (g/hr) | 41 | 39 |
| Activity ($g_{poly}/g_{catalyst}$) | 6900 | 1900 |

The use of inventive organosilica material supports dramatically increases the activity of Catalyst 1 (1,3-Me, BuCp)$_2$ZrCl$_2$) under similar reactor conditions and equal catalyst loadings as compared to the conventional silica supported catalyst. The more than threefold activity increase on a gram polymer per gram supported catalyst basis make organosilica catalysts supports particularly advantageous for use as a catalyst support for ethylene polymerization.

In certain aspects, the organosilica material catalyst supports prepared in accordance with certain aspects of the present disclosure increase a catalyst activity by greater than or equal to about 100% as compared to a convention support, or greater than about 150%, or greater than about 200%, or greater than about 250%, or greater than about 300%, and in certain variations, catalyst activity is increased by greater than about 350% as compared to activity of the same catalyst on a conventional catalyst support (e.g., SMAO support).

The oxygenate solution is prepared by adding known amounts, isopropanol and 1-octanol and n-hexadecane to anhydrous isohexane. The anhydrous isohexane is purchased from Aldrich and further dried over 3 Å molecular sieves. The solution is analyzed by GC to give a pre-adsorption chromatogram.

Example 10: Catalyst Activity During Polymerization with Organosilica Support Catalyst Systems A 2 L autoclave was heated to 110° C. and purged with N$_2$ at least 30 minutes. It was charged with dry NaCl (350 g; Fisher, S271-10 dehydrated at 180° C. and subjected to several pump/purge cycles and finally passed through a 16 mesh screen prior to use) and SMAO (5 g) at 105° C. and stirred for 30 minutes. The temperature was adjusted to 85° C. At a pressure of 2 psig N$_2$, dry, degassed 1-hexene (2.0 mL) was added to the reactor with a syringe then the reactor was charged with N$_2$ to a pressure of 20 psig. A mixture of H$_2$ and N$_2$ was flowed into reactor (200 SCCM; 10% H$_2$ in N$_2$) while stirring the bed.

Various solid catalysts indicated in Table 6 were injected into the reactor with ethylene at a pressure of 220 psig; ethylene flow was allowed over the course of the run to maintain constant pressure in the reactor. 1-hexene was fed into the reactor as a ratio to ethylene flow (0.1 g/g). Hydrogen was fed to the reactor as a ratio to ethylene flow (0.5 mg/g). The hydrogen and ethylene ratios were measure by on-line GC analysis. Polymerizations were halted after 1 hour by venting the reactor, cooling to room temperature then exposing to air. The salt was removed by washing with water two times; the polymer was isolated by filtration, briefly washed with acetone and dried in air for at least for two days.

TABLE 6

| Catalyst System Sample | Catalyst Compound | Catalyst Support Sample | Catalyst (mg) | Yield (g polyethylene) | Productivity (g/g cat) |
|---|---|---|---|---|---|
| Sample 11 | A | Sample 8 | 15.3 | 0 | 0 |
| Sample 14 | A | Sample 13 | 14.4 | 245.2 | 17028 |
| Sample 23 | J | Sample 12 | — | — | — |

This invention further relates to:

Embodiment BF

A catalyst system comprising (1) one or more olefin polymerization catalyst compounds, preferably coordination polymerization catalyst compounds; (2) a catalyst support comprising an organosilica material that is a polymer of at least one monomer of Formula

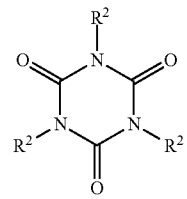

(VI)

where each R$^2$ is a Z$^{13}$OZ$^{14}$Z$^{15}$SiZ$^{16}$ group, and Z$^{13}$ represents a hydrogen atom, a C$_1$-C$_4$ alkyl group, or a bond to a silicon atom of another monomer unit; Z$^{14}$ and Z$^{15}$ each independently represent a hydroxyl group, a C$_1$-C$_4$ alkyl group, a C$_1$-C$_4$ alkoxy group, or an oxygen atom bonded to a silicon atom of another monomer unit; and Z$^{16}$ represents a C$_1$-C$_8$ alkylene group bonded to a nitrogen atom of the cyclic polyurea; and (3) an optional activator.

Embodiment BG

The process of Embodiment BF, where the organosilica material further comprises at least one monomer selected from the group consisting of: a) a monomer of Formula [Z$^1$OZ$^2$SiCH$_2$]$_3$ (I), wherein Z$^1$ represents a hydrogen atom, a C$_1$-C$_4$ alkyl group, or a bond to a silicon atom of another monomer and Z$^2$ represents a hydroxyl group, a C$_1$-C$_4$ alkoxy group, a C$_1$-C$_6$ alkyl group, or an oxygen atom bonded to a silicon atom of another monomer; b) a monomer of Formula Z$^3$OZ$^4$Z$^5$Z$^6$Si (II), wherein Z$^3$ represents a hydrogen atom or a C$_1$-C$_4$ alkyl group, or a bond to a silicon atom of another monomer; and Z$^4$, Z$^5$ and Z$^6$ are each independently selected from the group consisting of a hydroxyl group, a C$_1$-C$_4$ alkyl group, a C$_1$-C$_4$ alkoxy group, a nitrogen-containing C$_1$-C$_{10}$ alkyl group, a nitrogen-containing heteroaralkyl group, and a nitrogen-containing optionally substituted heterocycloalkyl group, and an oxygen atom bonded to a silicon atom of another monomer; c) a monomer of Formula Z$^7$Z$^8$Z$^9$Si—R$^1$—SiZ$^7$Z$^8$Z$^9$ (III), wherein Z$^7$ represents a hydroxyl group, a C$_1$-C$_4$ alkoxy group, or an oxygen atom bonded to a silicon atom of another comonomer; Z$^8$ and Z$^9$ each independently represent a hydroxyl group, a C$_1$-C$_4$ alkoxy group, a C$_1$-C$_4$ alkyl group, or an oxygen atom bonded to a silicon atom of another monomer; and R$^1$ is selected from the group consisting of a C$_1$-C$_8$ alkylene group, a C$_2$-C$_8$ alkenylene group, a C$_2$-C$_8$ alkynylene group, a nitrogen-containing C$_2$-C$_{10}$ alkylene group, an optionally substituted C$_6$-C$_{20}$ aralkyl and an optionally substituted C$_4$-C$_{20}$ heterocycloalkyl group; d) a trivalent metal oxide monomer of Formula M$^1$(OZ$^{10}$)$_3$ (IV), wherein M$^1$ represents a Group 13 metal and Z$^{10}$ represents a hydrogen atom, a C$_1$-C$_6$ alkyl or a bond to a silicon atom of another monomer; and e) a trivalent metal oxide monomer of Formula (Z$^{11}$O)$_2$M$^2$-O—Si(OZ$^{12}$)$_3$ (V), wherein M$^2$ represents a Group 13 metal and Z$^{11}$ and Z$^{12}$ each independently represent a hydrogen atom, a C$_1$-C$_6$ alkyl group, or a bond to a silicon atom of another monomer; and any combinations thereof.

Embodiment BH

A process to produce a polymer comprising i) contacting, in the gas phase or slurry phase, one or more olefin monomers, with the catalyst system of any of Embodiments BF-BG; and ii) obtaining a polymer.

All documents described herein are incorporated by reference herein, including any priority documents and/or testing procedures to the extent they are not inconsistent with this text.

What is claimed is:

1. A catalyst system comprising:
one or more olefin polymerization catalyst compounds;
a catalyst support comprising an organosilica material that is a polymer of at least one monomer of Formula $[Z^1OZ^2SiCH_2]_3$ (I), wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group, or an oxygen atom bonded to a silicon atom of another monomer; and
an activator.

2. The catalyst system of claim 1, wherein olefin polymerization catalyst compound is a coordination polymerization catalyst compound.

3. The catalyst system of claim 1, wherein $Z^2$ represents a hydroxyl group, a $C_1$-$C_4$ alkoxy group, or an oxygen atom bonded to a silicon atom of another monomer, and, optionally, $Z^1$ represents a hydrogen atom, methyl, ethyl or a bond to a silicon atom of another monomer.

4. The catalyst system of claim 1, wherein the polymer further comprises a second distinct monomer of Formula $[Z^1OZ^2SiCH_2]_3$ (I).

5. The catalyst system of claim 1, wherein the organosilica material further comprises at least one monomer selected from the group consisting of:
a monomer of Formula $Z^3OZ^4Z^5Z^6Si$ (II), wherein $Z^3$ represents a hydrogen atom or a $C_1$-$C_4$ alkyl group, or a bond to a silicon atom of another monomer; and $Z^4$, $Z^5$ and $Z^6$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, a nitrogen-containing optionally substituted heterocycloalkyl group, and an oxygen atom bonded to a silicon atom of another monomer;
a monomer of Formula $Z^7Z^8Z^9Si$—$R^1$—$SiZ^7Z^8Z^9$ (III), wherein $Z^7$ represents a hydroxyl group, a $C_1$-$C_4$ alkoxy group, or an oxygen atom bonded to a silicon atom of another monomer; $Z^8$ and $Z^9$ each independently represent a hydroxyl group, a $C_1$-$C_4$ alkoxy group, a $C_1$-$C_4$ alkyl group, or an oxygen bonded to a silicon atom of another monomer; and $R^1$ is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkylene and an optionally substituted $C_4$-$C_{20}$ heterocycloalkylene group;
a trivalent metal oxide monomer of Formula $M^1(OZ^{10})_3$ (IV), wherein $M^1$ represents a Group 13 metal and $Z^{10}$ represents a hydrogen atom, a $C_1$-$C_6$ alkyl or a bond to a silicon atom of another monomer;
a trivalent metal oxide monomer of Formula $(Z^{11}O)_2M^2$—O—$Si(OZ^{12})_3$ (V), wherein $M^2$ represents a Group 13 metal and $Z^{11}$ and $Z^{12}$ each independently represent a hydrogen atom, a $C_1$-$C_6$ alkyl group, or a bond to a silicon atom of another monomer;

a cyclic polyurea monomer of Formula

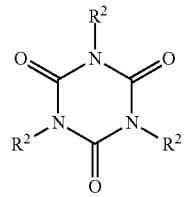

(VI)

wherein each $R^2$ is a $Z^{13}OZ^{14}Z^{15}SiZ^{16}$ group, wherein $Z^{13}$ represents a hydrogen atom, a $C_1$-$C_4$ alkyl group, or a bond to a silicon atom of another monomer; $Z^{14}$ and $Z^{15}$ each independently represent a hydroxyl group, a $C_1$-$C_4$ alkyl group, a $C_1$-$C_4$ alkoxy group, or an oxygen atom bonded to a silicon atom of another monomer; and $Z^{16}$ represents a $C_1$-$C_8$ alkylene group bonded to a nitrogen atom of the cyclic polyurea; and
combinations thereof.

6. The catalyst system of claim 1, wherein the catalyst support comprising an organosilica material has:
an average pore diameter between about 2 nm and about 50 nm;
a pore volume about 0.1 cm³/g to about 10 cm³/g; and/or
a surface area of about 100 m²/g to about 2,500 m²/g.

7. The catalyst system of claim 1, wherein the catalyst support comprising the organosilica material has an X-Ray diffraction spectrum exhibiting substantially no peaks above 4 degrees 2θ; and/or is made using substantially no added structure directing agent or porogen.

8. The catalyst system of claim 1, wherein the olefin polymerization catalyst compound comprises one or more metallocene compounds represented by the formula:

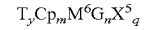

wherein each Cp is, independently, a cyclopentadienyl group which may be substituted or unsubstituted, $M^6$ is a Group 4 transition metal, G is a heteroatom group represented by the Formula $JR^*_z$ where J is N, P, O or S, and R* is a linear, branched or cyclic hydrocarbyl group having from one to twenty carbon atoms and z is 1 or 2, T is a bridging group, and y is 0 or 1, $X^5$ is a leaving group, and m=1 or 2, n=0, 1, 2 or 3, q=0, 1, 2 or 3, and the sum of m+n+q is equal to the oxidation state of the transition metal.

9. The catalyst system of claim 8, wherein each Cp is a cyclopentadienyl, indenyl or fluorenyl group, which may be substituted or unsubstituted, each $M^6$ is titanium, zirconium, or hafnium, and each $X^5$ is, independently, a halide, a hydride, an alkyl group, an alkenyl group or an arylalkyl group.

10. The catalyst system of claim 8, wherein y is 1, m is 1, n is 1, J is N, and R* is methyl, ethyl, propyl, butyl, pentyl, hexyl, heptyl, octyl, nonyl, cyclooctyl, cyclododecyl, decyl, undecyl, dodecyl, adamantyl or an isomer thereof.

11. The catalyst system of claim 8, wherein the at least one metallocene compound comprises one or more of: bis(tetrahydroindenyl)Hf Me₂; bis(1-butyl,3-methylcyclopentadienyl)ZrCl₂; bis-(n-butylcyclopentadienyl)ZrCl₂; (Dimethylsilyl)₂O bis(indenyl)ZrCl₂; dimethylsilyl(3-(3-methylbutyl)cyclopentadienyl)(2,3,4,5-tetramethylcyclopentadienyl) ZrCl₂; dimethylsilylbis(tetrahydroindenyl)ZrCl₂; dimethylsilyl-(3-phenyl-indenyl)(tetramethylcyclopentadienyl)ZrCl₂; dimethylsilyl(3-neopentylcyclopentadienyl)(tetramethylcyclopentadienyl)HfCl₂; tetramethyldisilylene bis (4-(3,5-di-tert-butylphenyl)-indenyl)ZrCl₂;

cyclopentadienyl(1,3-diphenylcyclopentadienyl)ZrCl$_2$; bis(cyclopentadienyl)zirconium dichloride; bis(pentamethylcyclopentadienyl)zirconium dichloride; bis(pentamethylcyclopentadienyl)zirconium dimethyl; bis(pentamethylcyclopentadienyl)hafnium dichloride; bis(pentanmethylcyclopentadienyl)zirconium dimethyl; bis(1-methyl-3-n-butylcyclopentadienyl)zirconium dichloride; bis(1-methyl-3-n-butylcyclopentadienyl)zirconium dimethyl; bis(1-methyl-3-n-butylcyclopentadienyl)hafnium dichloride; bis(1-methyl-3-n-butylcyclopentadienyl)hafnium dimethyl; bis(indenyl)zirconium dichloride; bis(indenyl)zirconium dimethyl; bis(tetrahydro-1-indenyl)zirconium dichloride; bis(tetrahydro-1-indenyl)zirconium dimethyl; dimethylsilylbis(tetrahydroindenyl)zirconium dichloride; dimethylsilylbis(tetrahydroindenyl)zirconium dimethyl; dimethylsilylbis(indenyl)zirconium dichloride; dimethylsilyl(bisindenyl)zirconium dimethyl; dimethylsilylbis(cyclopentadienyl)zirconium dichloride; and dimethylsilylbis(cyclopentadienyl)zirconium dimethyl.

12. The catalyst system of claim 1, wherein the activator comprises an alkylalumoxane and/or a non-coordinating anion.

13. The catalyst system of claim 1, wherein the one or more olefin polymerization catalyst compounds comprises a Ziegler-Natta catalyst compound.

14. The catalyst system of claim 1, wherein the one or more olefin polymerization catalyst compounds comprises one or more metallocene compounds of: dimethylsilyl (tetramethylcyclopentadienyl)(cyclododecylamido)titanium dimethyl; dimethylsilyl (tetramethylcyclopentadienyl)(cyclododecylamido)titanium dichloride; dimethylsilyl (tetramethylcyclopentadienyl)(t-butylamido)titanium dimethyl; dimethylsilyl (tetramethylcyclopentadienyl)(t-butylamido)titanium dichloride; μ-(CH$_3$)$_2$Si(cyclopentadienyl)(1-adamantylamido)M$^7$(R$^{15}$)$_2$; μ-(CH$_3$)$_2$Si(3-tertbutylcyclopentadienyl)(1-adamantylamido)M$^7$(R$^{15}$)$_2$; μ-(CH$_3$)$_2$Si(tetramethylcyclopentadienyl)(1-adamantylamido)M$^7$(R$^{15}$)$_2$; μ-(CH$_3$)$_2$C(tetramethylcyclopentadienyl)(1-adamantylamido)M$^7$(R$^{15}$)$_2$; μ-(CH$_3$)$_2$Si(tetramethylcyclopentadienyl)(1-tertbutylamido)M$^7$(R$^{15}$)$_2$; μ-(CH$_3$)$_2$Si(fluorenyl)(1-tertbutylamido)M$^7$(R$^{15}$)$_2$; μ-(CH$_3$)$_2$Si(tetramethylcyclopentadienyl)(1-cyclododecylamido)M$^7$(R$^{15}$)$_2$; or μ-(C$_6$H$_5$)$_2$C(tetramethylcyclopentadienyl)(1-cyclododecylamido)M$^7$(R$^{15}$)$_2$;

where M$^7$ is selected from a group consisting of Ti, Zr, and Hf and R$^{15}$ is selected from halogen or C$_1$-C$_5$ alkyl.

15. The catalyst system of claim 1, wherein the one or more olefin polymerization catalyst compounds comprises a first metallocene compound and a second metallocene compound independently selected from the group consisting of: SiMe$_2$(Me$_4$Cp)(cC$_{12}$N)TiMe$_2$ and bis(1-Bu,3-Me-Cp)ZrCl$_2$; SiMe$_2$(Me$_4$Cp)(cC$_{12}$N)TiMe$_2$ and (SiMe$_2$) bis(indenyl)ZrCl$_2$; SiMe$_2$(Me$_4$Cp)(cC$_{12}$N)TiMe$_2$ and (SiMe$_2$)$_2$O bis(indenyl)ZrCl$_2$; SiMe$_2$(Me$_4$Cp)(cC$_{12}$N)TiMe$_2$ and (SiMe$_2$)$_2$O bis(indenyl)ZrMe$_2$; SiMe$_2$(Me$_4$Cp)(cC$_{12}$N)TiMe$_2$ and SiMe$_2$(3-neopentylCp)((Me$_4$Cp)HfCl$_2$; SiMe$_2$(Me$_4$Cp)(cC$_{12}$N)TiMe$_2$ and SiMe$_2$(3-neopentylcyclopentadienyl)(Me$_4$Cp)HfMe$_2$; SiMe$_2$(Me$_4$Cp)(1-adamantylamido)TiMe$_2$ and bis(1-Bu,3-MeCp)ZrCl$_2$; and SiMe$_2$(Me$_4$Cp)(1-t-butylamido)TiMe$_2$ and bis(1-Bu,3-MeCp)ZrCl$_2$.

16. The catalyst system of claim 12, wherein the activator comprises methylalumoxane, ethylalumoxane, N,N-dimethylanilinium tetrakis(pentafluorophenyl) borate, triphenylcarbenium tetrakis(pentafluorophenyl)borate, N,N-dimethylanilinium tetrakis(perfluoronaphthyl)borate, triphenylcarbenium tetrakis(perfluoronaphthyl)borate or a mixture thereof.

17. A process to produce polymer comprising:
contacting, in the gas phase or slurry phase, one or more olefin monomers with the catalyst system of claim 1; and ii) obtaining a polymer.

18. The process of claim 17, wherein the polymer is an ethylene polymer or a propylene polymer.

19. The process of claim 17, wherein the process occurs at a temperature of from about 0° C. to about 300° C., at a pressure of from about 0.35 MPa to about 10 MPa, and at a time up to 300 minutes.

20. The process of claim 17, wherein the one or more olefin monomers comprise ethylene and one or more comonomer selected from propylene, butene, pentene, hexene, heptene, octene, nonene, decene, undecene, dodecene or a mixture thereof.

21. The process of claim 17, wherein the 2) catalyst support comprising an organosilica material comprises a plurality of mesopores having an average pore diameter between about 2 nm and about 50 nm and the polymerization occurs within the mesopores.

* * * * *